United States Patent
Kawamura et al.

[11] Patent Number: 6,166,807
[45] Date of Patent: Dec. 26, 2000

[54] METHOD OF URINALYSIS, URINALYSIS APPARATUS, METHOD OF MEASURING ANGLE OF ROTATION AND POLARIMETER

[75] Inventors: Tatsurou Kawamura, Tsuzuki-gun; Hiroshi Onishi, Hirakata; Nobuo Sonoda, Settsu, all of Japan

[73] Assignee: Matsushita Electric Industrial Co., Ltd., Osaka, Japan

[21] Appl. No.: 08/860,937

[22] PCT Filed: Nov. 15, 1996

[86] PCT No.: PCT/JP96/03368

§ 371 Date: Aug. 19, 1997

§ 102(e) Date: Aug. 19, 1997

[87] PCT Pub. No.: WO97/18470

PCT Pub. Date: May 22, 1997

[30] Foreign Application Priority Data

Nov. 16, 1995 [JP] Japan .................................... 7-298529
Nov. 29, 1995 [JP] Japan .................................... 7-310759

[51] Int. Cl.$^7$ ................................................ G01J 4/00
[52] U.S. Cl. ........................... 356/364; 356/368; 600/316
[58] Field of Search ..................... 356/364, 365, 356/366, 367, 368; 250/225; 600/316, 322

[56] References Cited

U.S. PATENT DOCUMENTS

| | | | |
|---|---|---|---|
| 3,312,141 | 4/1967 | Cary | 88/14 |
| 3,738,756 | 6/1973 | Chaney | 356/368 |
| 3,740,151 | 6/1973 | Chaney et al. | 356/117 |
| 4,035,083 | 7/1977 | Woodriff et al. | 356/368 |
| 4,725,140 | 2/1988 | Musha | 356/364 |
| 4,912,059 | 3/1990 | Newman et al. | |
| 4,988,199 | 1/1991 | Paul | 356/368 |
| 5,036,204 | 7/1991 | Leyden | 356/364 |
| 5,168,326 | 12/1992 | Tokieda et al. | 356/368 |
| 5,687,721 | 11/1997 | Kuhls | 356/364 |
| 5,871,442 | 2/1999 | Madarasz et al. | 356/364 |

FOREIGN PATENT DOCUMENTS

| | | |
|---|---|---|
| 27 24 543 | 12/1978 | Germany. |
| 41 28 458 | 3/1993 | Germany. |
| 42 42 232 | 6/1994 | Germany. |
| 55-112545 | 8/1980 | Japan. |
| 56-112667 | 9/1981 | Japan. |
| 61-286763 | 12/1986 | Japan. |
| 7-248367 | 9/1995 | Japan. |

*Primary Examiner*—Hoa Q. Pham
*Attorney, Agent, or Firm*—McDermott, Will & Emery

[57] ABSTRACT

The present invention provides a urinalysis apparatus easy to maintain and manage without using any supplies such as the test paper, in which the concentration of an optically active substance in urine is determined by measuring the angle of rotation of the urine. Also, a polarimeter and a urinalysis apparatus which are reliable, compact and inexpensive are provided by using a polarimeter including means for transmitting the polarized light through a specimen, applying a magnetic field to the specimen and detecting the change in the direction of light polarization due to the application of the magnetic field.

5 Claims, 23 Drawing Sheets

METHOD OF URINALYSIS, URINALYSIS APPARATUS, METHOD OF MEASURING ANGLE OF ROTATION AND POLARIMETER

TECHNICAL FIELD

The present invention relates to a method of measuring an angle of rotation usable for identifying, examining a purity and determining a concentration of a solute in the solution, and a polarimeter using the method, and more particularly to a method and an apparatus for urinalysis in which the angle of rotation of urine sampled from a man or other animal for examining the concentration of glucose, protein, etc. contained in the urine.

BACKGROUND ART

A healthy adult person usually voids 1000–1500 ml of urine every day. The total amount of solid components thereof is 50–70 g. About 25 g of the solid components is inorganic substances mainly composed of sodium chloride, potassium chloride and phosphoric acid, most of which are dissolved in the form of ions. The remains are organic substances mainly composed of urea and uric acid, and slight amounts of sugar and protein also exist therein. The concentrations of sugar and protein in the urine reflect the health conditions of the adult.

The sugar contained in the urine, i.e., glucose is discharged usually at a rate of 0.13–0.5 g per day into the urine. From this figure and the amount of urine, the concentration, i.e., the urine glucose level can be estimated at not more than 50 mg/dl on the average. The corresponding value is several hundred mg/dl, or sometimes as high as several thousand mg/dl. In other words, the value for diabetics can increase by a factor of ten or hundred as compared with the normal value.

On the other hand, the protein contained in urine, i.e., albumin is smaller in amount than glucose, and discharged at the rate of 3–60 mg into the urine. By taking the amount of the urine into account, average concentration is about 6 mg/dl or less. If a kidney is suffered, the albumin concentration reaches 100 mg/dl or more. That is, the value is increased to ten times the normal value or more.

Ordinally, as a conventional method of examining such sugar or protein in the urine, a test paper impregnated with an agent is dipped into the urine and a color reaction thereof is measured by spectrophotometer or the like.

In this method, however, different kinds of test paper were required to use for different items of examination including sugar, protein, etc. Also, a new test paper is required for each test, thereby leading to the disadvantage of a high running cost. Further, automation for labor saving has its own limit.

In addition, in a case of home use, a layman is demanded to set and change the test paper. This process is comparatively annoying and forms a stumbling block to the extension of the domestic use of the urinalysis apparatus.

Now, the conventional polarimeter will be explained. The conventional polarimeter had the problems described below.

An example of the conventional polarimeter is shown in FIG. 20.

In FIG. 20, a light source 121 is configured of a sodium lamp, a band-pass filter, a lens, a slit, etc. for projecting a substantially parallel light composed of a sodium D ray having a wavelength of 589 nm. A polarizer 122 is arranged in the direction of advance of the light projected from the light source 121 in such a position as to transmit only a component in a specific direction, which has a plane of vibration coincident with a transmission axis thereof, of the light projected from the light source 121. A sample cell 123 for holding a specimen is arranged in the direction of advance of the light transmitted through the polarizer 122. Further, an analyzer 124 is arranged, like the polarizer 122, in such a position as to transmit only the component of the light in a specific direction. An analyzer rotator 125 is for rotating the analyzer 124 on an axis parallel with the direction of advance of the light projected from the light source 121 under the control of a computer 127. A light sensor 126 is for detecting the light projected from the light source 121 and transmitted through the polarizer 122, the sample cell 123 and the analyzer 124. The computer 127 controls the analyzer rotator 125 while recording and analyzing a signal from the light sensor 126.

The principle of this conventional example will be explained with reference to FIG. 21. In the figure the abscissa represents the relative angle θ formed between the plane of vibration of the light transmitted through the polarizer 122 and the plane of vibration of the light transmitted through the analyzer 126. Herein, θ is assumed to take zero when the angle between these two planes of vibration reaches π/2, i.e., in the orthogonal nicol state. The ordinate represents an intensity I of the light that has reached the light sensor 126 based on an output signal of the light sensor 126. Herein, the solid line indicates the output signal in the case where the specimen exhibits no optical rotatory power. Under this condition, the relation between θ and I is shown by equation (1) mentioned below. Herein, a transmission loss and a reference loss of the s ample cell 123 and the analyzer 122 respectively are ignored.

$$I = T \times I_O \times (\cos \theta)^2 \qquad (1)$$

where,

T: transmittance of specimen $I_O$: intensity of light incident to specimen

As apparent from equation (1), I changes with a change of θ, i.e., with the rotation of the analyzer 126, so that an extinction point with a minimum I appears for each π.

In the case where the specimen has an optical rotatory power and its angle of rotation=α, on the other hand, the light intensity is represented by dashed line in FIG. 21 and given by equation (2).

$$I = T \times I_O \times \{\cos(\theta - \alpha)\}^2 \qquad (2)$$

As seen from this, a specimen having an optical rotatory power, as compared with a specimen having no optical rotatory power, has the angle associated with the extinction point displaced by α. The angle of rotation can be measured by finding the displacement α of the angle associated with the extinction point by the computer 127.

In this method, however, S/N ratio of the output signal of the light sensor 126 is comparatively inferior for lack of a modulated component and it is difficult to accurately determine the extinction point. As a result, a specimen with a small α cannot be measured with high accuracy.

For this reason, a polarimeter shown in FIG. 22 is also used in order to improve an accuracy of determining the extinction point. In FIG. 22, a light source 141 is configured of a sodium lamp, a band-pass filter, a lens, a slit, etc. for projecting a substantially parallel light of sodium D ray having a wavelength of 589 nm. A polarizer 142 and an analyzer 144 are arranged in the direction of advance of the light projected from the light source 141 aligning their transmission axes with the direction of advance of the light projected from the light source 141, with a sample cell holding a specimen interposed therebetween. An analyzer rotator 145 is for rotating the analyzer 144 on the transmission axis thereof as a rotation shaft under the control of a computer 147. A light sensor 146 detects the light projected from the light source 141 and transmitted through the polarizer 142, the sample cell 143 and the analyzer 144. The computer 147 controls the analyzer rotator 145, and records and analyzes the signal of the light sensor 146. An optical Faraday modulator 151 vibrates the direction of polarization. A signal generator 152 drives the optical Faraday modulator 151. A lock-in amplifier 143 is for phase sensitive detection of an output signal of the light sensor 146 with reference to the vibration-modulated signal from the optical Faraday modulator 151.

The operating principle of the polarimeter will be explained below with reference to FIG. 23.

In FIG. 23, the abscissa and the ordinate represent, as same in FIG. 21, $\theta$ and I, respectively, with the extinction point and the neighborhood thereof shown in an enlarged view. The optical Faraday modulator 151 vibration-modulates the direction of polarization with an amplitude of $\delta$ and an angular frequency of $\omega$. In the process, I is given as shown in equation (3) below from equation (2).

$$I = T \times I_O \times \{\cos(\theta - \alpha + \delta \times \sin(\omega \times t))\}^2 \quad (3)$$

where t: time

In FIG. 23, the extinction point or the neighborhood thereof is involved, i.e., $\theta \approx \pi/2$, and therefore equation (4) can be approximated as shown by equation (4).

$$\theta \approx \pi/2 + \beta \quad (4)$$

where, $|\beta| \ll 1$

Substituting this equation (4) into equation (3) gives equation (5) below.

$$I = T \times I_O \times \{[\sin(\beta - \alpha + \delta \times \sin(\omega \times t))]\}^2 \quad (5)$$

If it is assumed that an angle of rotation of the specimen and an amplitude of vibration. modulation are small, that is $|\alpha| \ll 1$ and $\delta \ll 1$, equation (5) is approximated as shown in equation (6) below.

$$I \approx T \times I_O \times \{\beta - \alpha + \delta \times \sin(\omega \times t)\}^2$$

$$= T \times I_O \times \{(\beta - \alpha)^2 + 2 \times (\beta - \alpha) \times \delta \times \sin(\omega \times t) + [\delta \times \sin(\omega \times t)]^2\}$$

$$= T \times I_O \times \{(\beta - \alpha)^2 + 2 \times (\beta - \alpha) \times \delta \times \sin(\omega \times t) + [\delta^2/2 \times (1 - \cos(2 \times \omega \times t))]\} \quad (6)$$

This indicates that the output signal I of the light sensor contains signal components of angular frequency=O (DC), $\omega$ and $2\times\omega$. This is obvious also from FIG. 15. By the phase sensitive detection of the value I with the vibration-modulated signal as a reference signal in the lock-in amplifier, it is possible to pick up the component of the angular frequency $\omega$, i.e., the value S shown in equation (7) below.

$$S = T \times I_O \times 2 \times (\beta - \alpha) \times \delta \quad (7)$$

This S is zero only when $\beta = \alpha$ and this point constitutes an extinction point. In other words, the value of $\beta$ when S becomes zero in a step of rotating the analyzer and sweeping $\beta$ is the angle $\alpha$ of rotation.

As described above, modulation of the direction of polarization, makes it possible to pick up the signal of the modulated frequency component selectively by separating it from noises such as a source light intensity, power fluctuations and radiation, thereby making it possible to obtain the signal S with high S/N. This value S can be used to determine the extinction point accurately and permits a highly accurate measurement of the angle a of rotation.

Nevertheless, the above-mentioned polarimeter is complicated in structure due to the need of a means for rotating the analyzer and a modulator, and therefore has its own limit of cost reduction and reliability.

DISCLOSURE OF INVENTION

Taking these subjects into consideration, the object of the present invention is to provide a method of urinalysis easy to maintain and manage without using supplies such as a test paper. Further, the object of the present invention is to provide a reliable, compact and inexpensive polarimeter and a urinalysis apparatus using this one.

According to the method of urinalysis of the present invention, a concentration of an optically active substance contained in urine is determined by measuring an angle of rotation of the urine. Glucose and protein existing in the urine exhibit an optical rotatory power whereas urea and uric acid constituting the main components of the organic substances in the urine have no optical rotatory power. Also, none of the inorganic substances in the urine exhibits the optically rotatory power. For this reason, the concentration of glucose or protein in the urine can be accurately determined by measuring the angle of rotation of the urine. Similarly, the concentration of L-ascorbic acid (what is called vitamin C) which may be contained in the urine can also be determined by measuring the angle of rotation. Once the angle of rotation of the urine is measured by using a high-precision polarimeter, therefore, the angle of rotation due to the optically active substances like glucose and protein existing in low concentration can be detected thereby making it possible to calculate the concentration of these substances. As a result, the concentration of the glucose and protein in the urine can be examined without using any supplies.

The present invention provides a highly accurate, reliable, compact and inexpensive polarimeter which solves the above-mentioned problems of the conventional polarimeter.

The principle of a method of analyzing the urine by measuring the angle of rotation according to the invention will be explained below.

The angle A of rotation is proportional to the product of a specific angle a of rotation and the concentration C of an optically active substance. This relation is shown by equations (8) and (9).

In the case where only one type of optically active substance is involved, the relation is given by $$A \text{ [degree]} = L \text{ [cm]} \times a \times C \text{ [kg/dl]} \quad (8)$$

while if N types of optically active substances are contained, the relation holds:

$$A = L \times (a_1 \times C_1 + a_2 \times C_2 \ldots + a_N \times C_N) \quad (9)$$

where L is the measured optical path length.

The specific angles a of rotation of glucose and albumin are shown in Table 1.

TABLE 1

| wavelength | 589 nm | 580 nm |
|---|---|---|
| glucose | 50 | 25 |
| albumin | −60 | −10 |

Unit: [degree/cm·dl/kg]

The specific angles of rotation shown above are values for a glucose aqueous solution and an albumin aqueous solution at 20° C.

Specifically, when a light having a wavelength of 589 nm propagates by the distance of 10 cm through the glucose aqueous solution of 100 g/dl in concentration, a direction of polarization of the light rotates by 50 degrees. Although this concentration cannot be achieved due to the limited solubility of glucose actually, the direction of polarization rotates by $50 \times 10^{-3}$ degrees at the concentration of 100 mg/dl since the angle of rotation and the concentration are in proportion as shown in equation (8).

In the case where glucose is the only optically active substance in the urine, therefore, a urine glucose level can be calculated from the specific angle of rotation of glucose by measuring the angle of rotation of the urine. A similar calculation is possible also for albumin and L-ascorbic acid.

Further, an angle of rotation of urine having a known range of angle of rotation presented by an interfering optically active substance other than optically active substance of unknown concentration is measured, and the concentration C of the optically active substance is determined to be within the range of $$(A-A_h)/(\alpha \times L) \leq C \leq (A-A_l)/(\alpha \times L) \quad (10)$$

where

A: measured angle of rotation of the urine [degree], $A_h$: maximum value of the angle of rotation presented by the interfering optically active substance [degree], $A_l$: minimum value of the angle of rotation presented by interfering optically active substance [degree], α: specific angle of rotation of the optically active substance [degree/cm·dl/kg], and L: measurement optical path length [cm].

According to this method, the concentration of each of a plurality of optically active substances including glucose, albumin, L-ascorbic acid, etc., which may coexist in urine can be calculated.

First, equation (9) is modified to obtain equation (11) below.

$$A = A_x + A_d \quad (11)$$

where it is assumed that $A_x = L \times \alpha_1 \times C_1$, and $A_d = L \times (\alpha_2 \times C_2 + \ldots + \alpha_N \times C_N)$.

In equation (2), assume that substance 1 is an optically active substance X to be detected, and substances 2–N are other optically active substances, i.e., interfering optically active substances, $A_d$ corresponds to the angle of rotation presented by the interfering optically active substances. If the concentration range of the substances 2 to N is known, the maximum value $A_h$ and the minimum value $A_l$ that $A_d$ can assume are known. This leads to equation (12) below.

$$A - A_h \leq A_x = A - A_d \leq A - A_l \quad (12)$$

Equation (12) determines the range of the angle $A_x$ of rotation, and the concentration $C_x$ is also determined from the specific angle $\alpha_x$ of rotation and the length L of the measurement optical path. Equation (12) is expressed as equation (10) in terms of the concentration C of the optically active substance X.

In the case where the glucose concentration in urine is examined, for example, assume that the concentration of the interfering albumin is not more than 10 mg/dl, i.e., assume that the minimum value of the albumin concentration which can be assumed is 0 and the maximum value thereof is 10 mg/dl, respectively, with the wavelength of 589 nm and the length of measurement light path of 10 cm, $A_h$ is zero degree and $A_l$ is $-6 \times 10^{-3}$ degrees. Then, assuming that measurement A=0.1 degree, the glucose concentration C (mg/dl) can be determined to be $200 \leq C \leq 212$ from Table 1.

Actually, considering the fact that an abnormal urine glucose level can reach not less than several hundred mg/dl, the examination with the above-described accuracy often suffices. Specifically, in the case where the albumin concentration is about 10 mg/dl or less representing a normal value, the abnormality of the sugar in the urine can be determined by measuring the angle of rotation with a single wavelength.

Further, angles of rotation of the urine including N types of optically active substances is measured using the light having N different types of wavelength thereby to determine the concentrations of the optically active substances in the urine. The specific angle of rotation varies with wavelength due to optically rotatory dispersion. Consequently, in the case where N types of optically active substances coexist, N independent simultaneous equations can be obtained using equation (9) by measuring the angle of rotation by each of the N wavelengths. This makes it possible to calculate the concentration for N types of optically active substances.

In this way, the abnormality of the sugar or the albumin concentration in the urine can be determined by measuring the angle of rotation of the urine.

Also, the angle of rotation of the urine for the light having a wavelength of not less than 500 nm is measured. For the short wavelength of less than 500 nm, the absorption due to urochrome (a yellow component of urine), principally, increases to such an extent that the measurement accuracy is sometimes adversely affected.

Further, the concentration of a light-scattering substance contained in the urine is determined by measuring an amount of a light scattered in the urine.

Also, the light scattering substance is at least one of protein and blood. The molecular weight of the albumin constituting protein in the urine is about 70 thousands, which causes light scattering sufficiently large as compared with the light scattering due to the molecular weight of other organic substances including glucose (having a molecular weight of about 180) or the like and inorganic substances contained in the urine. Specifically, the scattering of the light propagating in the urine is dominated by albumin. As a result, the albumin concentration can be determined by irradiating light to the urine and observing the scattered light directly or in the form of the decreasing amount of the transmitted light. It is also possible to examine the presence or absence of the blood which have comparatively large particles.

Further, the amount of the scattered light in the urine is measured for the light having a wavelength of not less than 500 nm. As in the case of measuring the specific angle of rotation, the light having a wavelength of shorter than 500 nm involves an increased absorption mainly due to urochrome, often adversely affecting the measurement accuracy.

Furthermore, the amount of the scattered light is measured together with the angle of rotation of the urine thereby to determine the concentration of the light scattering substances as well as the optically active substances contained in the urine. This is effective especially in the case where both glucose and albumin exist in an amount not negligible in the urine.

In this way, according to the present invention, the concentration of sugar and protein in the urine can be easily and accurately determined by measuring the angle of rotation of the urine. This method also eliminates the need of supplies such as the test paper unlike in the prior method.

In addition, a high reliability and a low cost of the polarimeter is made possible, and a reduced cost and a higher reliability of the urinalysis apparatus is also made possible as described below.

According to the method of measuring the angle of rotation of the present invention, an angle of rotation of a specimen is measured by applying a magnetic field to the specimen and detecting the change in the direction of polarization of the light due to the magnetic field.

In view of this, the present invention provides a polarimeter comprising a monochromatic light source for projecting the light, a polarizer for transmitting only the polarized component in a specific direction of the projected light, a sample cell for holding the specimen and arranged in such a manner that the light passed through the polarizer is transmitted through the specimen, means for applying a magnetic field to the specimen, means for sweeping the magnetic field, an analyzer for transmitting only the polarized component in a specific direction of the light transmitted through the specimen, a light sensor for detecting the light transmitted through the analyzer, and calculation means for calculating an angle of rotation of the specimen on the basis of a magnetic field sweep signal of the magnetic field sweeping means and an output signal of the light sensor.

When a light is propagated through a medium and a magnetic field is applied in the direction of propagation of the light, the direction of polarization of the light is rotated in accordance with the propagation. This phenomenon is called the optical Faraday effect. This optical Faraday effect is given by equation (13) below.

$$a = V \times H \times L \tag{13}$$

where a: rotational angle of the direction of polarization [minute],

V: Verdet's constant of the medium [minute/A],

H: magnetic field [A/m], and

L: propagation distance [m].

The value V in equation (13) is varied with the medium, light wavelength and temperature. An example of V for various media is shown in Table 2.

TABLE 2

|  | V/100 [minute/A] |
| --- | --- |
| water | 1.645 |
| chloroform | 2.06 |
| acetone | 1.42 |

TABLE 2-continued

|  | V/100 [minute/A] |
| --- | --- |
| rock crystal | 2.091 |
| flint glass | 4.85 |

Temperature = 20° C.
Wavelength = 589 nm

This optical Faraday effect is utilized by the optical Faraday modulator used in the prior art. This is such that a solenoid coil is wound on a rod of flint glass and is supplied with a current to apply a magnetic field thereto, thereby modulating the direction of polarization of the light propagated in the direction of the magnetic field. Free modulation can be conducted by controlling the current flowing in the solenoid coil.

As described above, the optical Faraday effect permits the modulation of the polarization direction upon application of a magnetic field to a medium. As apparent from Table 2, this is also the case with water, chloroform, acetone or the like widely used as a solvent. Therefore, upon application of a magnetic field to a solution with a specimen dissolved therein, the very solution rotates the direction of polarization of the light propagating through the solution by the optical Faraday effect. Specifically, once a magnetic field is applied to a sample cell holding a specimen, the particular sample cell and the magnetic field application means function as an optical Faraday modulator. A solenoid coil, a magnet etc. which apply the magnetic field in the direction of light propagation can be used as a magnetic field application means. The magnetic field can be modulated by modulating the current flowing in the solenoid coil or by modulating the distance between the magnet and the specimen. In this way, the direction of polarization can be vibration-modulated by vibration-modulating the magnetic field, thereby making it possible to measure the angle of rotation in the same manner as in the prior art.

Also, if the magnetic field is swept, i.e., if the applied magnetic field is changed from a given strength to a different strength (including a change in polarity of the magnetic field), then the direction of polarization of the magnetic field can be rotated. By doing so, the same effect can be obtained as if the analyzer is rotated. Specifically, unlike in the prior art in which the displacement of the extinction point with the rotation of the analyzer is directly read from the angle of the analyzer, the method of measuring the angle of rotation according to the present invention is such that the displacement of the extinction point with the magnetic field swept is read by a current value, for example, which is converted into a magnetic field and further into an angle, thereby measuring the angle of rotation of the specimen. This is substantially the same as if a magnetic field is detected in which the angle of rotation generated by an optically active substance of a specimen coincides with the rotational angle of the direction of polarization due to the optical Faraday effect caused by an application of the magnetic field.

Sweeping of the magnetic field is not necessarily limited to a continuous change of strength but includes a discrete change thereof. In view of the fact that a change in the characteristic of an output signal of a light sensor with the rotation of the direction of polarization is generally known, the angle of rotation can be calculated by measurements taken at two or more points and interpolation or extrapolation from the measurements. Specifically, the angle of rotation of a specimen can be calculated from the output signals of the light sensor for at least two different magnetic fields. In such a case, the measurement time can be shortened.

BEST MODE FOR CARRYING OUT THE INVENTION

Preferred embodiments of the invention will be described below in detail.

<<Embodiment 1>>

A first embodiment will be explained in detail below.

Figure 1:
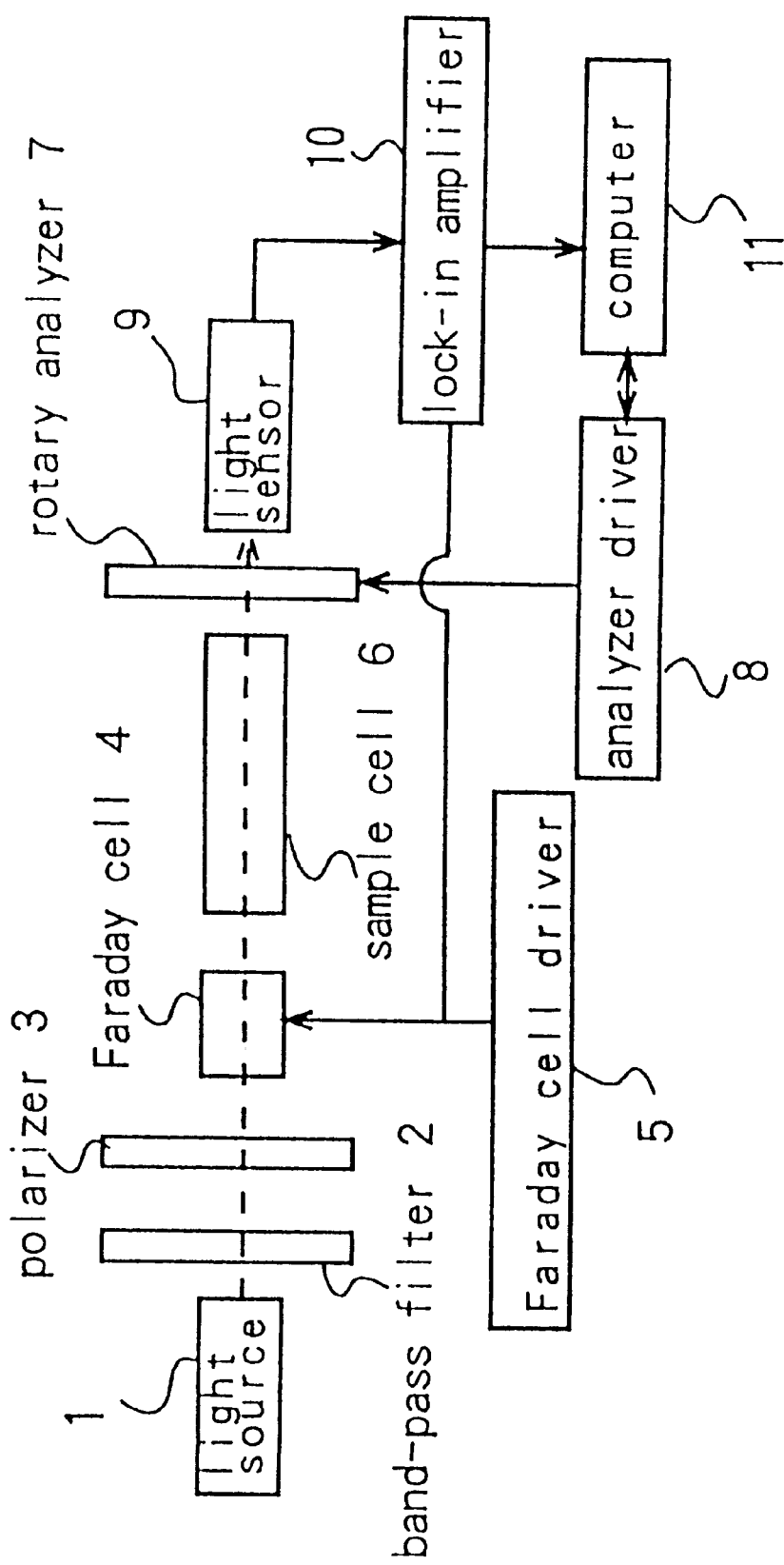
FIG. 1 is a schematic diagram showing a configuration of a polarimeter used in an embodiment of the present invention.

FIG. 1 is a diagram showing a configuration of a polarimeter used in the present embodiment. The basic principle of this polarimeter is the optical zero-order method based on the vibration of the plane of polarization using the Faraday effect.

A low-pressure 180 W sodium lamp 1 emits a parallel light. A band-pass filter 2 transmits only the components having a wavelength of 589.0 nm of the light emitted from the sodium lamp 1. A polarizer 3 passes specific component of the polarized light from the band-pass filter 2 which have a plane of vibration parallel to the page, for example. A modulated signal current input from a Faraday cell driver 5 causes the Faraday cell 4 to modulate the direction of polarization of the transmitted light by a very small width due to the optical Faraday effect. The substantial length of the light path of a sample cell 6 for containing the urine is 10 cm. A rotary analyzer 7, like the polarizer 3, passes only specific polarized component of the light transmitted through the sample cell 6, but can be set at an arbitrary angle by an analyzer driver 8. A light sensor 9 detects the light transmitted through the rotary analyzer 7 and outputs a signal based on the intensity of the light thus detected. A lock-in amplifier 10 subjects the output of the light sensor 9 to phase sensitive detection with the modulated signal applied to the Faraday cell 4 as a reference signal. A computer 11 applies to the analyzer driver 8 an instruction for continuously rotating the rotary analyzer 7 while recording the output of the lock-in amplifier 10. As a result, the angle of the rotary analyzer 7 at which the output of the lock-in amplifier 10 becomes zero is found to calculate the angle of rotation. With the above-mentioned configuration, the accuracy of about $10^{-3}$ is achieved.

The urine was analyzed as described below using this polarimeter.

Figure 2:
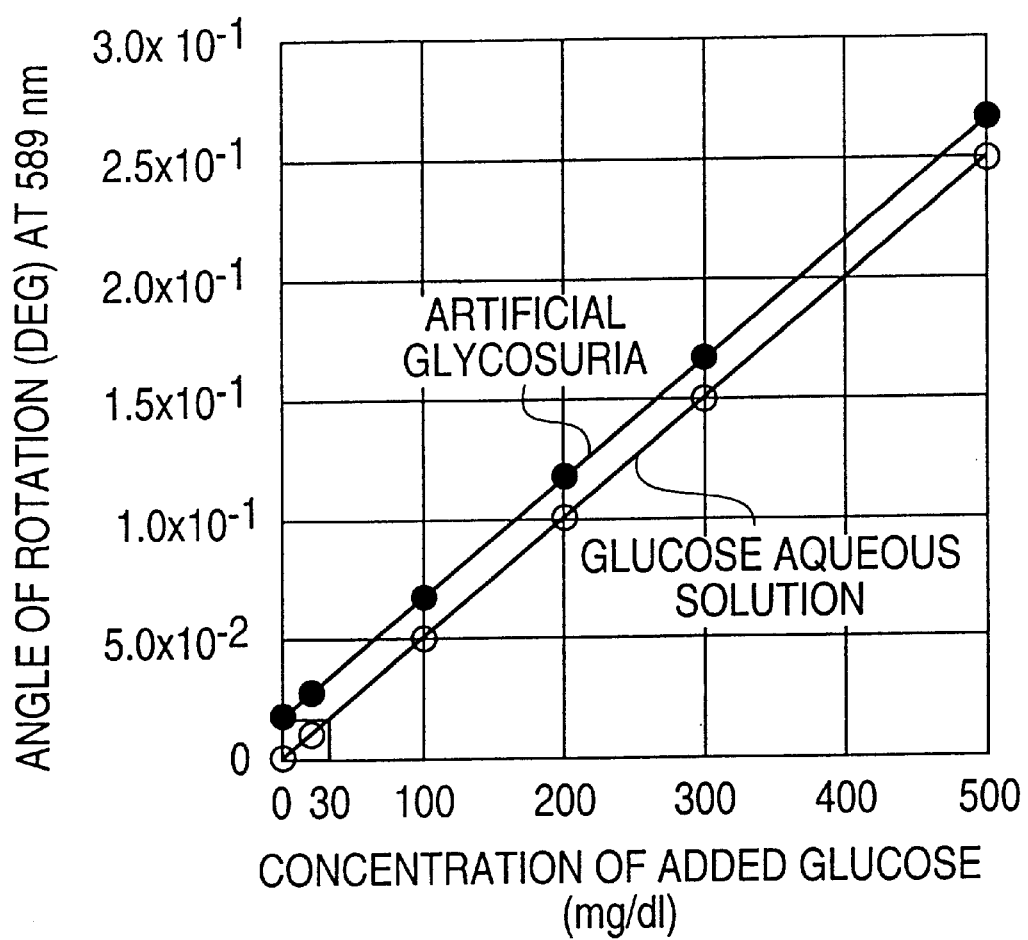
FIG. 2 is a characteristic diagram showing the relation between a glucose concentration of an aqueous solution of glucose or urine with glucose dissolved therein and an angle of rotation obtained by a measurement using the same polarimeter.

First, in order to confirm the performance of the polarimeter, an analytical curve was plotted as described below. Pure water was placed into a sample cell 6, and the angle of the rotary analyzer 7 was measured at which the output of the lock-in amplifier 10 becomes zero. At this time, the polarizer 3 and the rotary analyzer 7 are in the orthogonal nicol state. With this angle as a reference and with the pure water as a solvent, the angle of rotation was measured of glucose aqueous solutions prescribed with concentrations of 20, 100, 200, 300 and 500 mg/dl, respectively. The result is shown by white circles in FIG. 2. This indicate that the glucose concentration can be measured.

Then, the angle of rotation was measured of the urine determined to have a glucose concentration of 50 mg/dl or less and an albumin concentration of 10 mg/dl or less by the urinalysis made in advance using the test paper. Further, with this urine as a solvent, glucose solutions having concentrations of 20, 100, 200, 300 and 500 mg/dl, respectively, in other words, artificial glycosuria were prepared, and the angle of rotation of these were measured. The result is shown by black circles in FIG. 2. The angle of rotation of these artificially-prepared glycosuria is represented by a straight line translated in parallel from the analytical curve by $1.5 \times 10^{-2}$ degrees and accurately reflects the glucose concentrations.

The angle of rotation of the urine itself was $1.5 \times 10^{-2}$ degrees. This, combined with the range of albumin concentration obtained in advance by urinalysis, can decide from equation (10) the glucose concentration C as $$30 \text{ mg/dl} \leq C \leq 42 \text{ mg/dl}$$

This coincides with the result of analysis obtained beforehand.

Further, the angle of rotation was measured similarly of the urine determined by an urinalysis apparatus to have a glucose concentration of 30 mg/dl or more and a normal albumin concentration, i.e., 10 mg/dl or less. As a result, this urine exhibited the angle of rotation of $2.2 \times 10^{-1}$ degrees. This, combined with the range of albumin concentration obtained in advance by the urinalysis apparatus, shows that the glucose concentration C is $$440 \text{ mg/dl} \leq C \leq 452 \text{ mg/dl}$$

This also coincides with the result of analysis obtained in advance.

In this way, for the urine having a normal albumin concentration, an abnormal glucose concentration of the urine (urine glucose level) can be accurately detected by measuring the angle of rotation. For example, the glucose concentration of 300 mg/dl or more can be determined with an error of about 12 mg/dl.

As described above, according to this embodiment, the urine glucose level can be examined without using any supplies such as test paper, thereby greatly contributing to practical effects.

<<Embodiment 2>>

Explanation will be made about a method of analyzing the urine containing both glucose and albumin in an amount not negligible.

Figure 3:
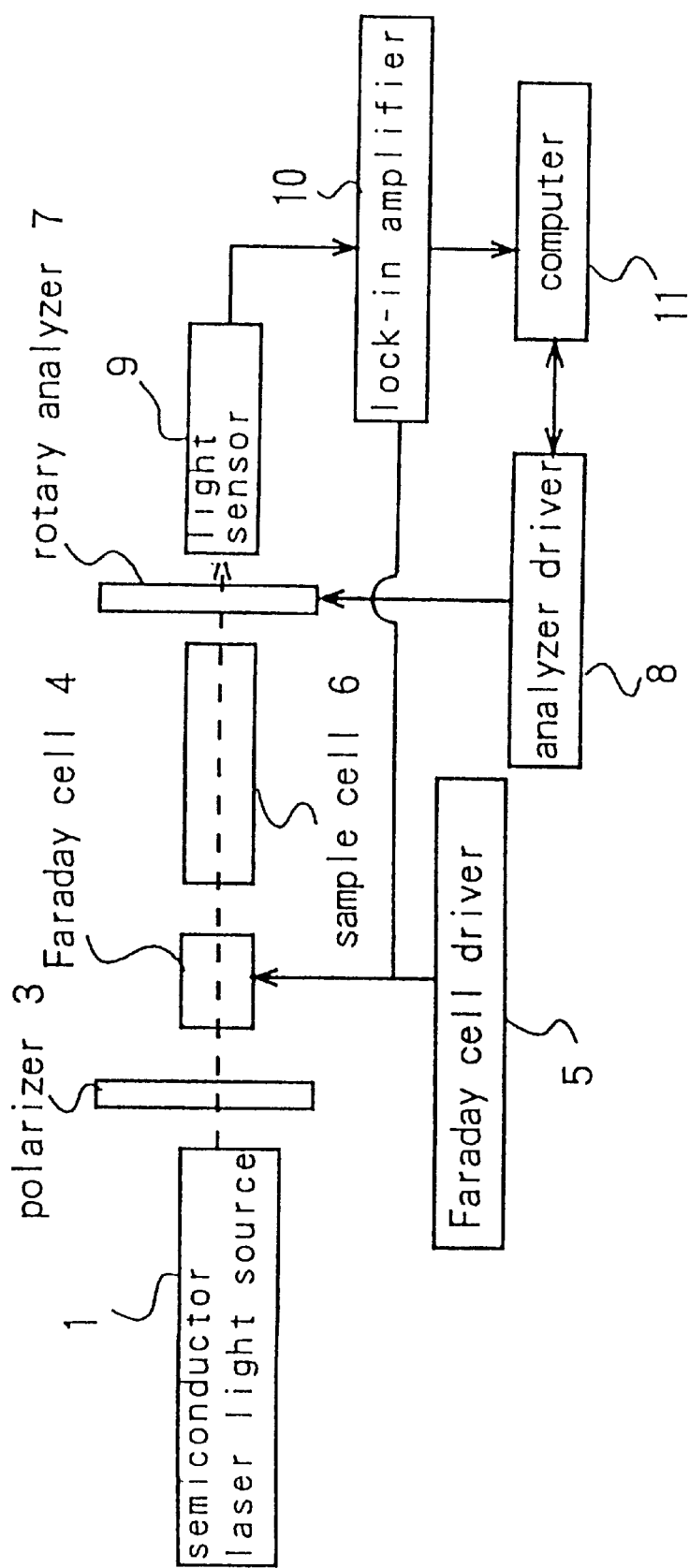
FIG. 3 is a schematic diagram showing a configuration of a polarimeter used in another embodiment of the present invention.

According to this embodiment, a polarimeter shown in FIG. 3 was used together with the polarimeter shown in the first embodiment. This polarimeter, like the polarimeter of the first embodiment, operates on the basic principle of the optical zero-order method based on the vibration of the plane of polarization using the Faraday effect. Numerals 3 to 11 designate the same components as the corresponding ones used in the first embodiment. But, a semiconductor laser light source 12 was used in place of the sodium lamp. The semiconductor laser light source 12 projects a parallel light of 5 mW having an emission wavelength of 830 nm. This polarimeter operates in the same manner as the corresponding one of the first embodiment and achieved the accuracy of about $10^{-3}$ degrees.

Figure 4:
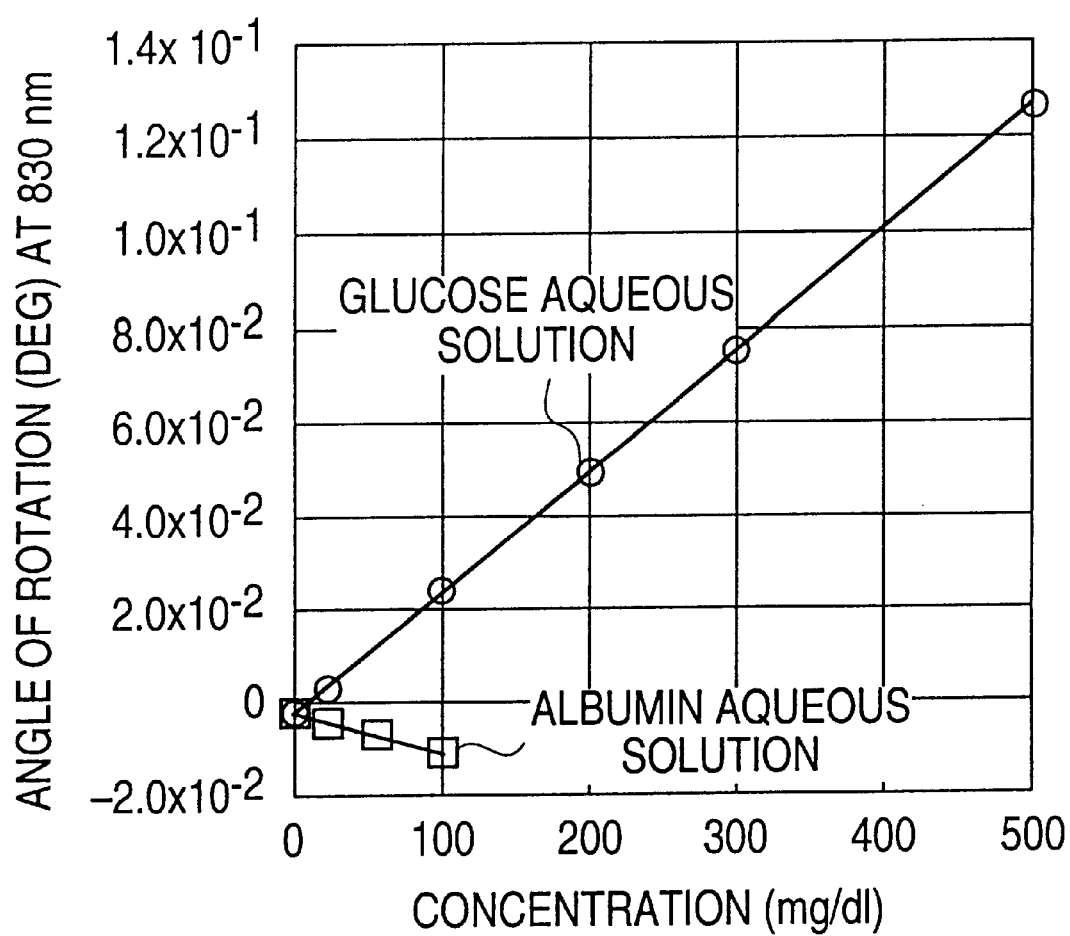
FIG. 4 is a characteristic diagram showing the relation between a glucose concentration of glucose aqueous solution or an albumin concentration of an albumin aqueous solution and the angle of rotation for the light having a wavelength of 830 nm obtained by a measurement using the same polarimeter.

First, in order to confirm performance of this polarimeter, an analytical curve was prepared. With pure water placed in a cell, the angle of the rotary analyzer 7 was measured at which the output of the lock-in amplifier 10 becomes zero. On the other hand, glucose aqueous solutions having concentrations of 20, 100, 200, 300 and 500 mg/dl, respectively, and albumin aqueous solutions having concentrations of 20, 50 and 100 mg/dl, respectively, were prepared. With the angle of the analyzer for the pure water as a reference, the angle of rotation of these aqueous solutions were measured. The result is shown in FIG. 4. This indicates that the angle of rotation thus measured can be approximated linearly with respect to the concentration of glucose or albumin. In other words, it was confirmed that the concentration is possible to measure.

Figure 5:
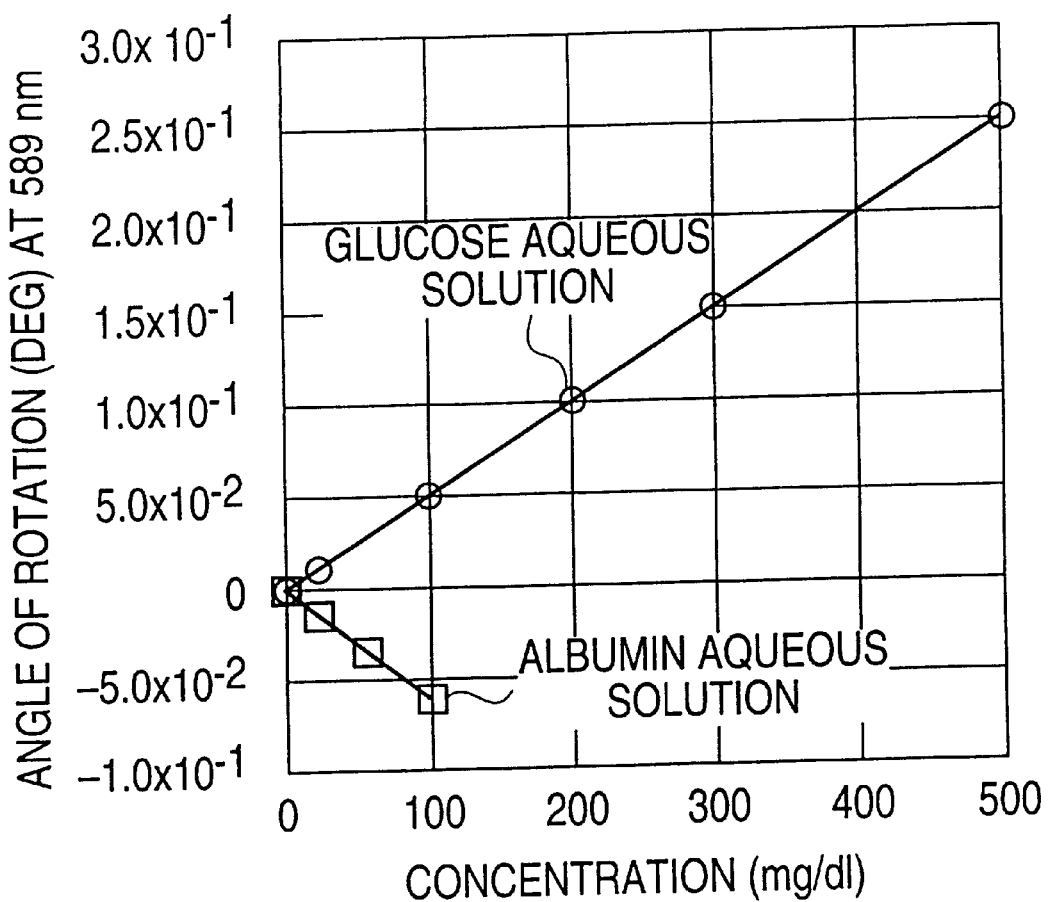
FIG. 5 is a characteristic diagram showing a relation between concentrations of the same aqueous solutions and angles of rotation for a light having a wavelength of 589 nm.

Then, the same specimens were measured by a polarimeter using a light source having a wavelength of 589 nm as in the first embodiment. The result is shown in FIG. 5.

Equation (9) and the specific angles of rotation in Table 1 give simultaneous equations shown in equations (14) and (15). Let the glucose and albumin concentrations be $C_1$ and $C_2$ [kg/dl], respectively:

$$A_{589} = 0.1 \times (50C_1 - 60C_2) \quad (14)$$

$$A_{830} = 0.1 \times (25C_1 - 10C_2) \quad (15)$$

where $A_{589}$: angle of rotation [degrees] for the light having a wavelength of 589 nm, and $A_{830}$: angle of rotation [degrees] for the light 830 nm in wavelength. Measurement of $A_{589}$ and $A_{830}$ makes possible calculation of two unknown figures $C_1$ and $C_2$ from equations (14) and (15), respectively.

In fact, an aqueous solution containing 100 mg albumin and 300 mg glucose per dl was prepared and the angle of rotation of this aqueous solution was measured in the same manner. The result was $$A_{589} = 9.0 \times 10^{-2} \text{ [degrees]}$$

$$A_{830} = 6.5 \times 10^{-2} \text{ [degrees]}$$

The simultaneous equations (14) and (15) were solved using this result, and it was confirmed that the result coincides with the loading ratio between albumin and glucose.

In similar fashion, the angle of rotation was measured of the urine which had been decided to have a glucose concentration of 50 mg/dl or less and an albumin concentration of 100 mg/dl or more as a result of the conventional urinalysis using the test paper. The measurement shows that the angle of rotation $A_{589}$ for the wavelength of 589 nm and the angle of rotation $A_{830}$ for the wavelength of 830 nm were $$A_{589} = -6 \times 10^{-2} \text{ [degrees]}$$

$$A_{830} = -5 \times 10^{-3} \text{ [degrees]}$$

Equations (14) and (15) were solved using this result thereby to obtain a glucose concentration of 30 mg/dl and an albumin concentration of 125 mg/dl. This coincides with the result of the conventional urinalysis.

Also, the angle of rotation was measured of the urine which had been decided to have a glucose concentration of 300 mg/dl or more and an albumin concentration of 100 mg/dl or more. As a result, the angles of rotation $A_{589}$ and $A_{830}$ were determined as $$A_{589} = 1 \times 10^{-1} \text{ [degrees]}$$

$$A_{830} = 8 \times 10^{-2} \text{ [degrees]}$$

Equations (14) and (15) were solved using this result thereby to obtain a glucose concentration of 380 mg/dl and an albumin concentration of 150 mg/dl. This coincides with the result of the conventional urinalysis.

As described above, according to this embodiment, in the case where both glucose and albumin exist in the urine to an extent not negligible, the urine glucose level and the albumin concentration thereof can be examined without using any supplies such as the test paper by determining the angles of rotation using a plurality of light having different wavelengths.

<<Embodiment 3>>

In this embodiment, a method will be explained for examining the albumin concentration in the urine and a bloody urine by the light scattering action.

Figure 6:
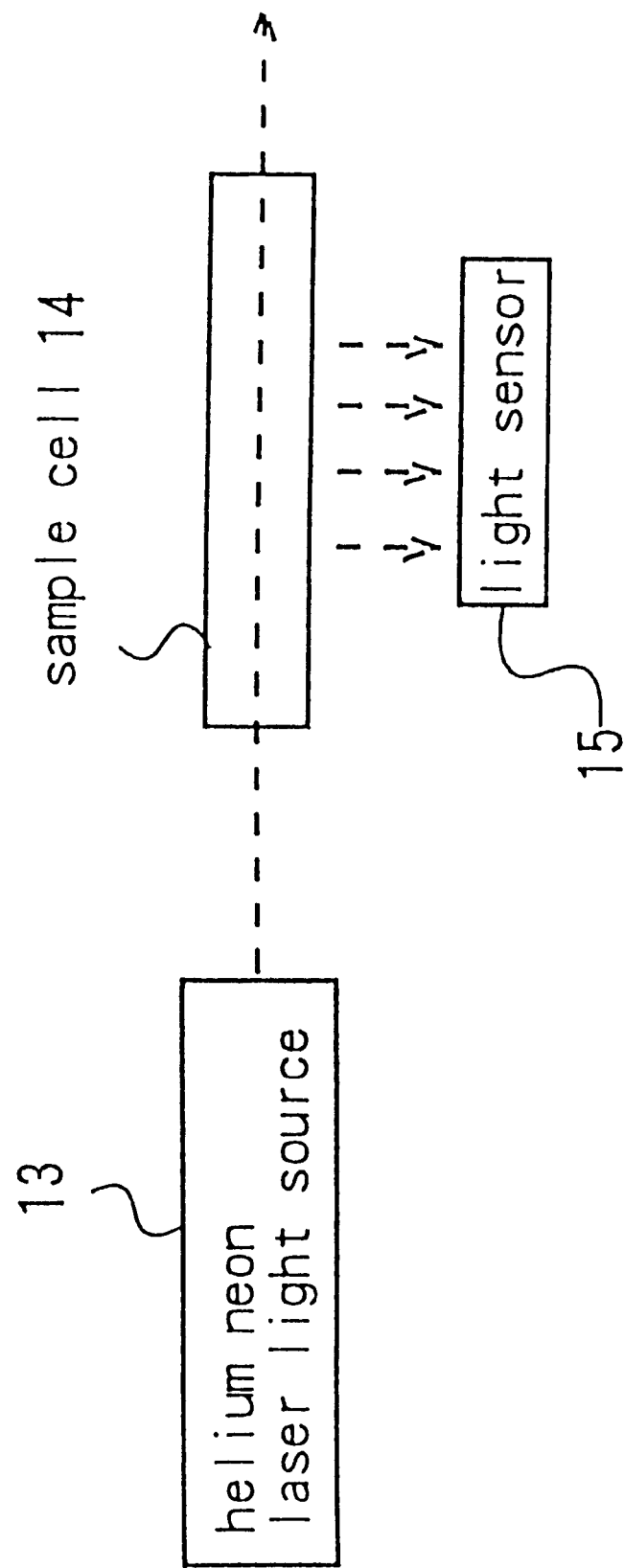
FIG. 6 is a schematic diagram showing a configuration of a scattered light amount measuring instrument used in another embodiment of the present invention.

A urinalysis apparatus according to this embodiment will be explained below with reference to FIG. 6. A helium neon laser 13 is adapted to project parallel light 5 mW in output having a wavelength of 633 nm onto a sample cell 14 containing the urine. The sample cell 14 has a substantial light path length of 10 cm and a width of 1 cm. Since the sample cell 14 has the two transparent sides, a scattered light in direction perpendicular to the light path can pass outward of the sample cell 14. A light sensor 15 is arranged with the angle of visibility thereof coinciding with the sample cell 14 and capable of detecting the scattered components of the laser light propagating in the urine.

Figure 7:
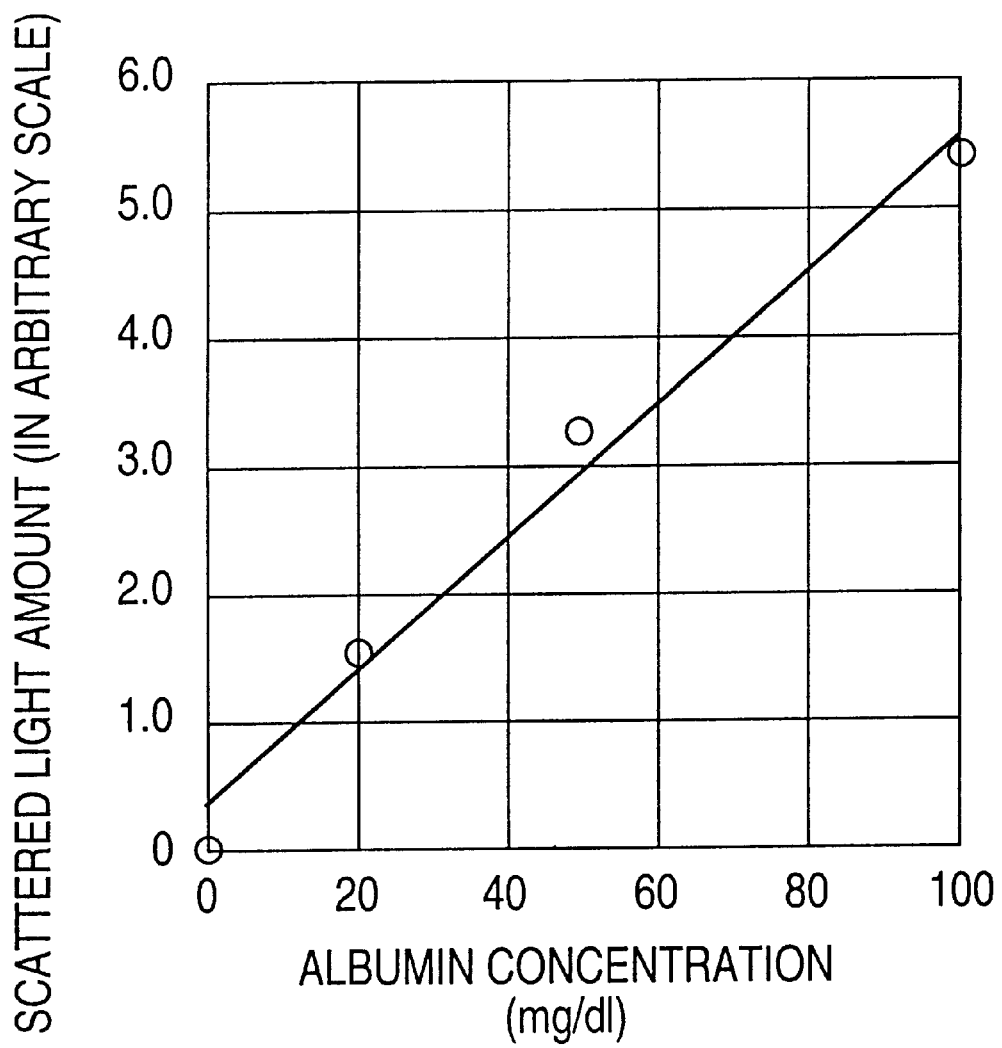
FIG. 7 is a characteristic diagram showing a relation between a concentration of an albumin aqueous solution and a scattered light amount obtained by using the same measuring instrument.

Albumin aqueous solutions of 20, 50 and 100 mg/dl in concentration, respectively, were prepared, and the scattered light amount of these solutions and pure water were measured. The result is shown in FIG. 7. In this way, a positive correlation was confirmed between the albumin concentration and the scattered light amount.

Then, the scattered light amount was measured of the urine that had been decided to have a glucose concentration of 50 mg/dl or less and an albumin concentration of 10 mg/dl or less by the analysis using the test paper, but the scattered light could not be detected. A measurement of the urine that had been decided to have a glucose concentration of 300 mg/dl or more and an albumin concentration of 10 mg/dl or more by the conventional urinalysis method, on the other hand, confirmed the presence of a signal of about 6 on the scale in FIG. 7. Further, a signal of about e could also be confirmed by another measurement of an urine that had been decided to have a glucose concentration of 50 mg/dl or less and an albumin concentration of 100 mg/dl or more by the conventional urinalysis method. In the process, the scattered light amount was measured on an arbitrary scale.

As described above, the albumin concentration can be determined by measuring the amount of the scattered components of the light propagating in the urine. In this way, scattering of the light due to comparatively large particles such as albumin or blood is sufficiently large as compared with the scattering of the light due to glucose or other organic or inorganic substances in the urine. In other words, scattering of the light propagating in the urine due to albumin and blood is controlling. Consequently, it is possible to determine the albumin concentration or the blood concentration in the urine by irradiating light into the urine and observing the amount of scattered light.

As explained above, according to this embodiment, the presence of large particles such as albumin and blood can be examined without using any supplies like the test paper, thereby greatly contributing to practical effects.

<<Embodiment 4>>

In this embodiment, a method of urinalysis will be explained in which both an angle of rotation and an amount of scattered light propagating in urine are measured at the same time. This examination method is effective especially in the case where the amounts of glucose and albumin existing in urine are both not negligible. Also, according to this embodiment, unlike in the third embodiment, the scattered light amount is observed in terms of the decrease in the transmitted light amount.

In this embodiment, the polarimeter shown in FIG. 3 and explained in the second embodiment is used as it is. The principle of measuring the angle of rotation is similar to that for the second embodiment.

Now, a method of measuring the transmitted light amount, i.e., a method of substantially measuring the scattered light amount will be explained.

While rotating a rotary analyzer 7 is continuously, an output of a lock-in amplifier 10 is recorded. Then, the output change of the lock-in amplifier 10 for each predetermined rotational angle of the rotary analyzer 7 can be detected. This output change amount corresponds to the transmitted light amount. This output change amount is standardized by the measurement value obtained for pure water thereby to determine the scattered light amount in urine.

This method can determine the angle of rotation and the scattered light amount at the same time in a single measurement process, and it is thus possible to determine the concentration of a light-scattering substance such as albumin. In other words, the range of concentration of albumin and the like required in advance in the first embodiment can be grasped, and therefore the glucose concentration can also be determined.

As described above, according to this embodiment, the glucose concentration and the albumin concentration in the urine can be examined at the same time with a simple configuration and a single measurement, thereby greatly contributing to practical effects.

Another method available for measuring the amount of the scattered light is to temporarily fix the rotary analyzer 7 at a predetermined angle and to determine the amount from an associated output value of the lock-in amplifier 10.

A similar effect can of course be obtained by directly detecting the scattered light from the side of the sample cell 6 as in the third embodiment.

Figure 8:
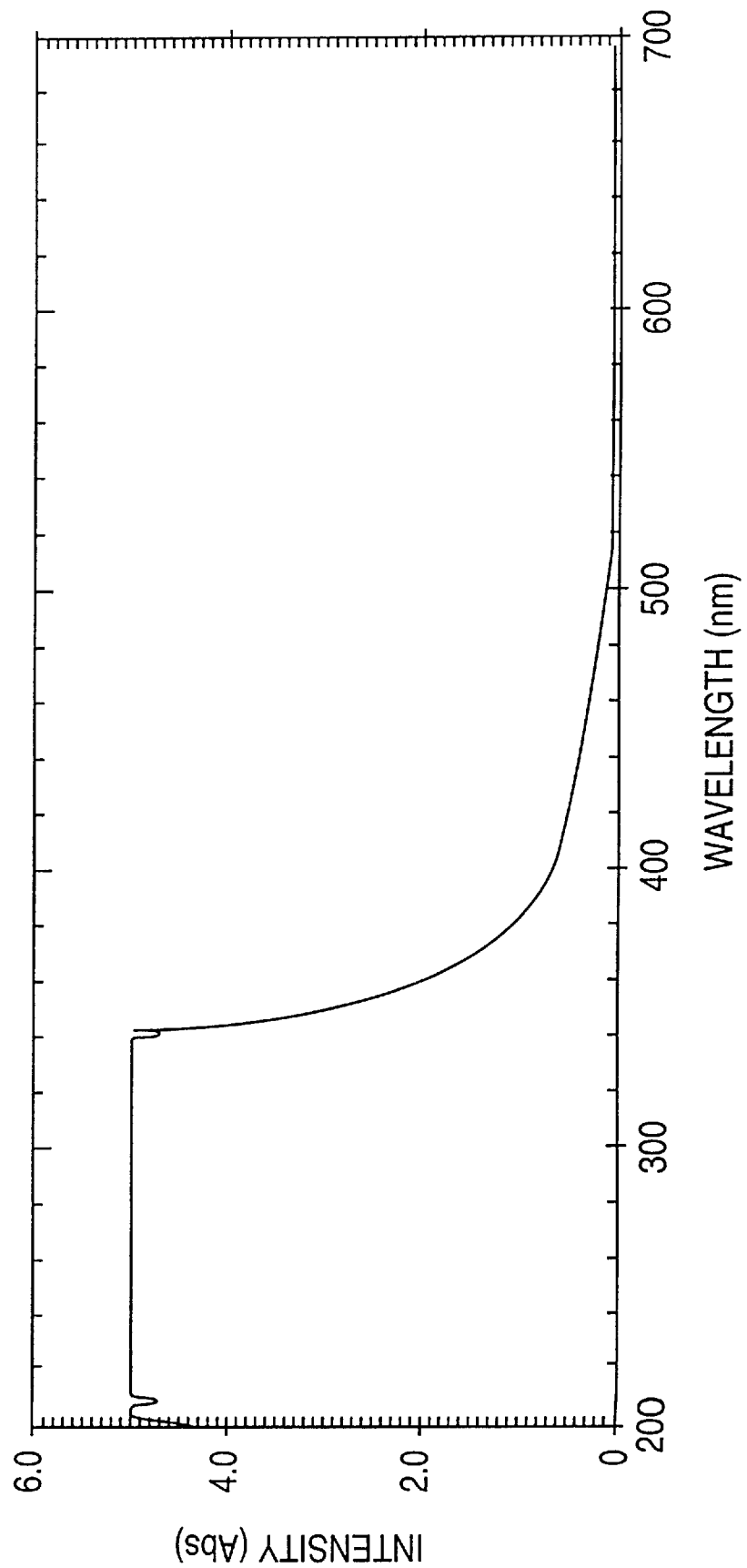
FIG. 8 is a characteristic diagram showing a relation between a wavelength of the incident light and an intensity of a light transmitted through the urine.

As described above, according to this invention, it is possible to provide a urinalysis method which is easy to maintain and manage without using any supplies such as the test paper. The angle of rotation increases, however, with the decrease in the wavelength of the measured light due to the optically rotatory dispersion until the appearance of an abnormal dispersion. Consequently, although the light of a shorter wavelength can be used more advantageously for high accuracy measurement, the light having a wavelength of about 500 nm or more is more desirable for urinalysis. This is by reason of the fact that as obvious from FIG. 8 showing the spectral characteristic of normal urine, the light having a wavelength shorter than 500 nm is absorbed increasingly by urochrome (a yellow component contained in the urine), sometimes deteriorating the measurement accuracy. For similar reason, the desirable wavelength of the light used for measuring the scattered light amount is 500 nm or more due to the absorption of urochrome.

The embodiments described above concern a method of determining the glucose concentration and the albumin concentration in urine by projecting monochromatic light on the urine and determining the angle of rotation of the urine or the amount of the light scattered in the urine. The polarimeters used for the urinalysis, however, have the problem of a low reliability and a high cost as described above. In view of this, detailed description will be made below about a polarimeter higher in reliability and lower in cost than the conventional polarimeters and the urinalysis apparatus using such a polarimeter.

<<Embodiment 5>>

Figure 9:
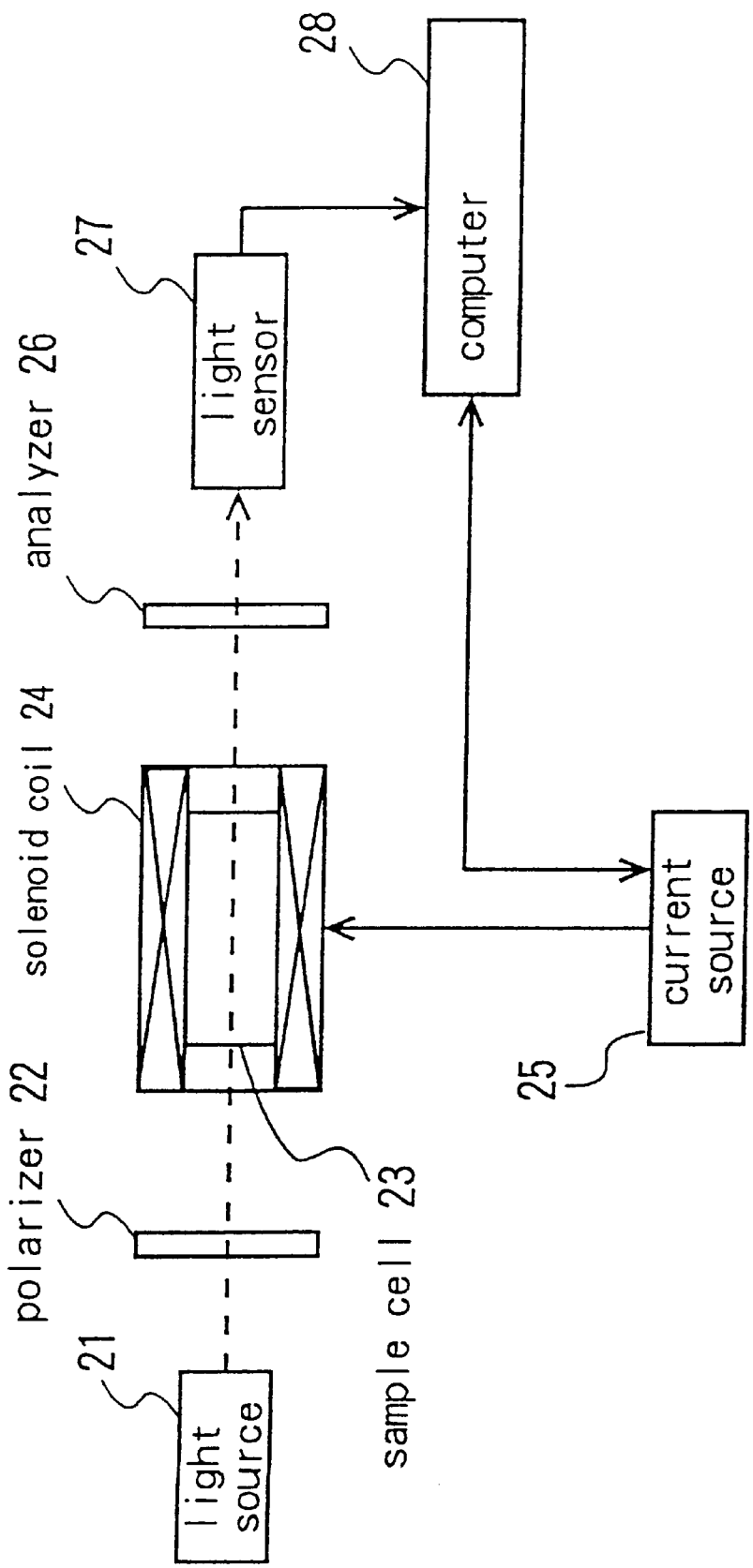
FIG. 9 is a schematic diagram showing a configuration of a polarimeter used in another embodiment of the invention.

A configuration of a polarimeter according to this embodiment is shown in FIG. 9. A light source 21 configured of a 180 W low-pressure sodium lamp, a band-pass filter, a lens, a slit, etc. for projecting substantially parallel light is adapted to project a sodium D ray having a wavelength of 589.0 nm. Of all the light rays projected from the light source 21, a polarizer 22 allows only the component in a specific direction having a plane of vibration parallel to the transmission axis to pass therethrough. A specimen is held in a cylindrical sample cell 23 of glass. The sample cell 23 is arranged in such a position that the substantially parallel light projected from the light source 21 and polarized by being passed through the polarizer 22 enters and passes along the direction of the central axis thereof. The substantial light path length of this sample cell 23 is 300 mm.

A solenoid coil 24 wound around the sample cell 23 applies a magnetic field substantially uniformly to the sample cell 23 and the specimen held therein in the direction of propagation of the light by the current from the current source 25. Specifically, a current of 1 A applied to the solenoid coil 24 causes a magnetic field H of $5 \times 10^3$ A/m. The current source 25 can supply a current of −5 A to 5 A to the solenoid coil 24. The analyzer 26 is arranged in such a position as to transmit only those components of the light transmitted through the sample cell 23 which are polarized in the direction perpendicular to the page, in other words in orthogonal nicol state with the polarizer 22. A light sensor 27 detects the light transmitted through the analyzer 26. A computer 28 issues a command signal to the current source 25 to record and analyze on output signal of the light sensor 27.

Figure 10:
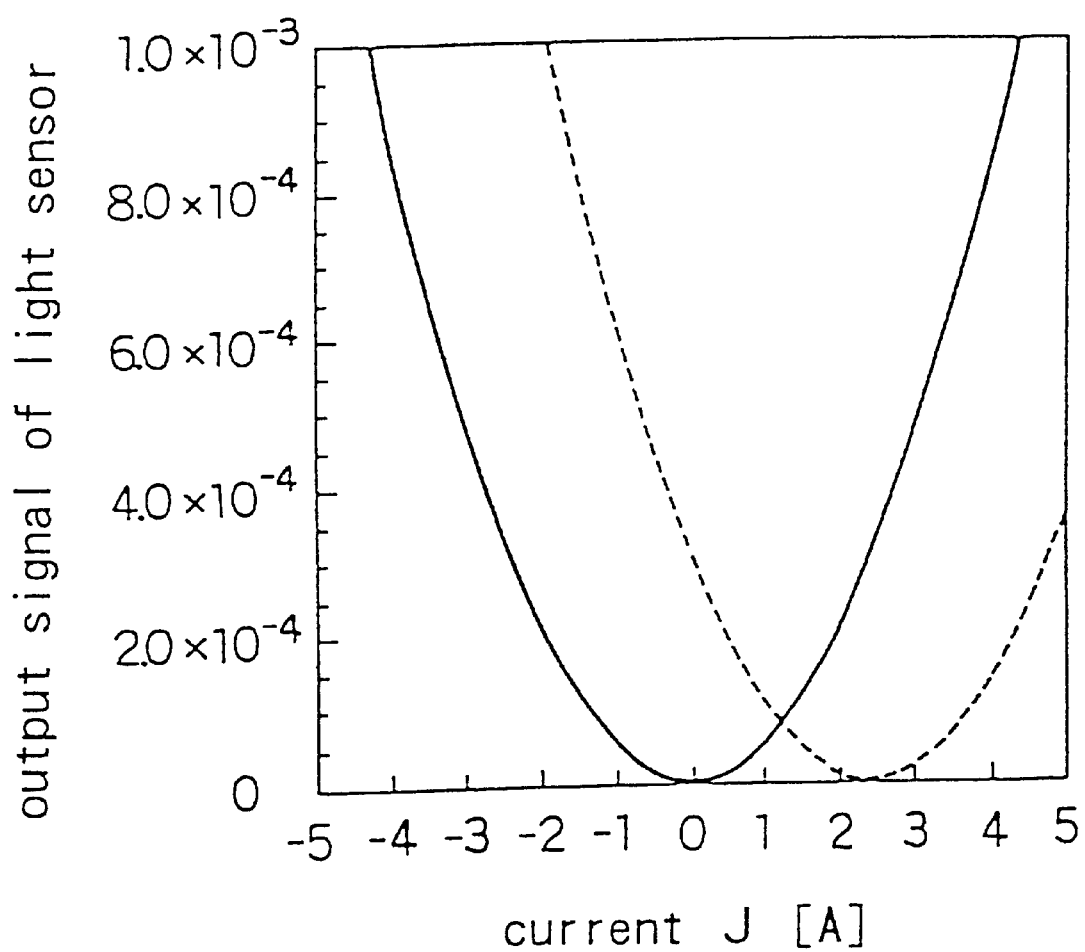
FIG. 10 is a characteristic diagram showing a relation between the amount of the current flowing in a solenoid coil and an output signal of the light sensor obtained by using the same polarimeter.

The operation of this polarimeter will be explained. The computer 28 issues a command signal to the current source 25 so that the current flowing in the solenoid coil 24 is swept from −5 A to 5 A. The output signal of the light sensor 27 produced in the process is shown in FIG. 10. In FIG. 10, the abscissa represents a current J flowing in the solenoid coil 24, and the ordinate represents an output signal (arbitrary value) of the light sensor 27.

The solid line is associated with the case in which the pure water exhibiting no optical rotatory power is measured as a specimen. In this case, since the relative angle between a transmission axis of the polarizer 22 and a transmission axis of the analyzer 26 is π/2, an extinction point appears, when J=0, i.e., when the magnetic field is not applied to the pure water constituting the specimen and there occurs no rotation of the direction of polarization of the light which otherwise might be caused by the optical Faraday effect. When J is changed, the output signal of the light sensor 27 changes according to equation (13) in a manner similar to the case where the analyzer is rotated in the conventional polarimeter. In the polarimeter in this embodiment, however, J corresponds to β in equation (4).

The dotted line in the drawing shows a cane sugar aqueous solution of 20° C. in temperature and 500 mg/dl in concentration as a specimen. In this case, the extinction point appears at J=2.4 A. Specifically, the curve is obtained by translating the curve indicated by the solid line in the drawing horizontally along the abscissa by +2.4 A. This 2.4 A displacement of the extinction point is caused by the angle of rotation of the specimen. This polarimeter determines the angle of rotation of the specimen from the magnitude of this displacement.

The function of the polarimeter according to this embodiment was quantitatively confirmed using the aqueous solution of cane sugar. The angle of rotation a and the specific angle of rotation [α] are given as follows:

$$\alpha = [\alpha]/10000 \times L \times C \quad (16)$$

where

L: distance of propagation=light path length of sample cell [m], and

C: concentration of aqueous solution [mg/dl].

The specific angle of rotation [α] of cane sugar for the light having a wavelength of 589 nm is 66.5 degrees for the aqueous solution at 20° C. Therefore, the angle of rotation α for this cane sugar aqueous solution when L=0.3 and C=500 is α≈1 degree from equation (16).

Then, the rotational angle a of the direction of polarization due to the optical Faraday effect is calculated from equation (13) in the manner mentioned below.

From the characteristics of the solenoid coil 24, the magnetic field H is given as $1.2 \times 10^4$ A/m when J=2.4 A. This and Verdet's constant V of water shown in Table 2 are substituted into equation (13) to give $$a = 1.645 \times 10^{-2} \times 1.2 \times 10^4 \times 0.3$$
$$= 59.22 \text{ [minutes]} \approx 1°$$

This confirms that the angle of rotation of the specimen coincides with the rotational angle due to the optical Faraday effect.

Figure 11:
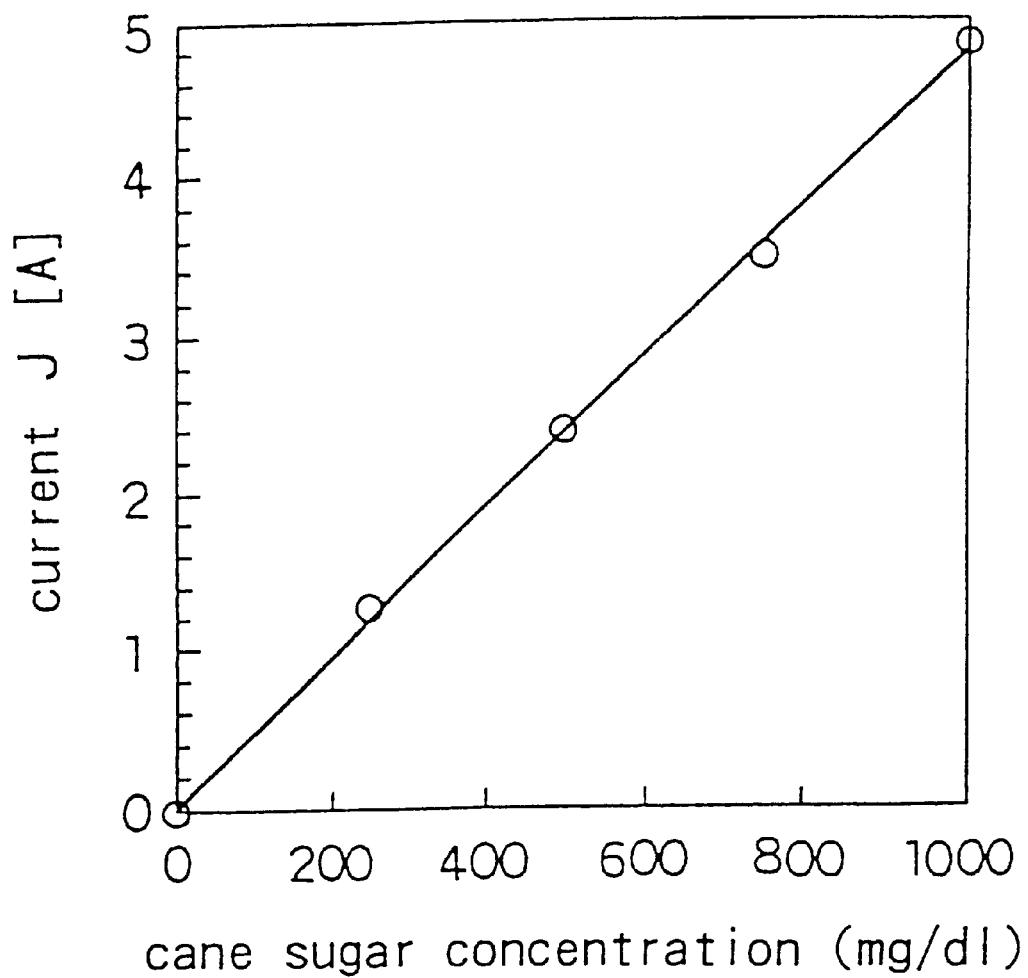
FIG. 11 is a characteristic diagram showing a relation between a concentration of an aqueous solution of cane sugar and the output signal of the light sensor obtained by using the same polarimeter.

Further, using this polarimeter, the angle of rotation was measured of the cane sugar aqueous solution having the concentrations of 250, 750 and 1000 mg/dl, respectively, at the temperature of 20° C. The result is shown in FIG. 11. In the figure, the abscissa represents the cane sugar concentration, and the ordinate represents the current J when an extinction point appears. This is indicative of the fact that the output signal of the light sensor can be approximated linearly with respect to the cane sugar concentration.

The conventional polarimeter measures the displacement of an extinction point, i.e., the angle of rotation of a specimen by rotating an analyzer and reading the angle of the analyzer directly. In the polarimeter according to the present embodiment, on the other hand, as described above, a magnetic field is applied to the specimen with being swept and the displacement of the extinction point is read in terms of current. This current value is converted into a magnetic field intensity and further into an angle thereby to calculate the angle of rotation of the specimen.

As described above, according to this embodiment, a magnetic field is applied to the specimen and swept, thereby eliminating the need of means for rotating the analyzer. Consequently, it is possible to realize a reliable, compact and inexpensive polarimeter of a very high practical value. In sweeping the magnetic field, the intensity is not necessarily changed continuously but can be changed discretely. Since the characteristic of the output signal of the light sensor changing with the rotation of the direction of polarization is known as shown in equation (2), the angle of rotation can be calculated by measuring the magnetic field intensity at least two points and by interpolation or extrapolation of the measurements. This process is especially effective for shortening the measurement time.

<<Embodiment 6>>

Figure 12:
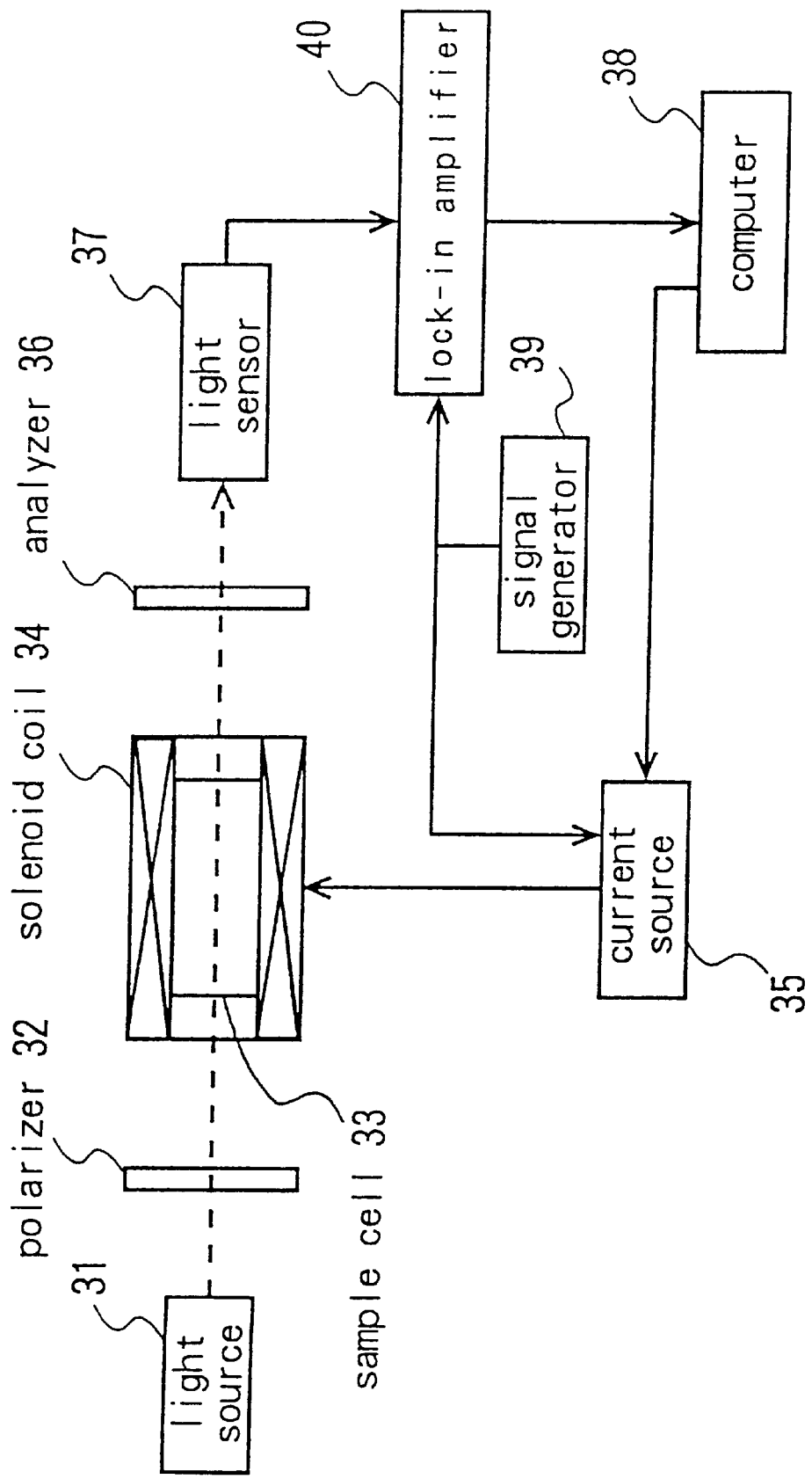
FIG. 12 is a schematic diagram showing a configuration of a polarimeter according to still another embodiment of the present invention.

The polarimeter according to this embodiment will be explained with reference to FIG. 12. A light source 31 similar to the one used in the fifth embodiment projects the sodium D ray having a wavelength in 589.0 mm. A polarizer 32 allows only the polarized light component in a specified direction, for example, only those polarized light components that are parallel to the page to transmit. A cylindrical sample cell 33 for holding the specimen is made of glass and has a substantial light path length of 50 mm.

The analyzer 36 is arranged in such an orthogonal nicol state with the polarizer 32 that only the polarized light components perpendicular to the page are transmitted. A light sensor 37 detects the light transmitted through the analyzer 36. A computer 38 issues a command signal to a current source 35, while recording and analyzing the output signal of the light sensor 37. Also, the computer 38 issues a command signal to the current source 35 and causes the current flowing in the solenoid coil 34 to be swept up from −5 A to 5 A. The solenoid coil 34 has a structure substantially similar to the one used in the fifth embodiment, and applies a magnetic field H of $5 \times 10^3$ A/m to the sample cell 33 with a current of 1 A. A signal generator 39 supplies a vibration-modulated signal to the current source 35. The current source 35 converts the vibration-modulated signal into a vibration-modulated current signal, and superimposes it on the sweeping current commanded by the computer 38, then the resulting current obtained is applied to the solenoid coil 34. In this polarimeter, the 1.3 kHz modulated signal is converted into a vibration-modulated current signal having an amplitude of 0.02 A, which is supplied to the solenoid coil 34. The lock-in amplifier 40 phase-sensitively detects the output signal of the light sensor 37 with reference to the vibration-modulated signal of the signal generator 39. The output signal of the lock-in amplifier 40 corresponds to the angular frequency component $\omega$ of the output signal of the light sensor 37 in equation (6), i.e., S shown in equation (7). The extinction point, therefore, corresponds to the time when the value S becomes zero.

Figure 13:
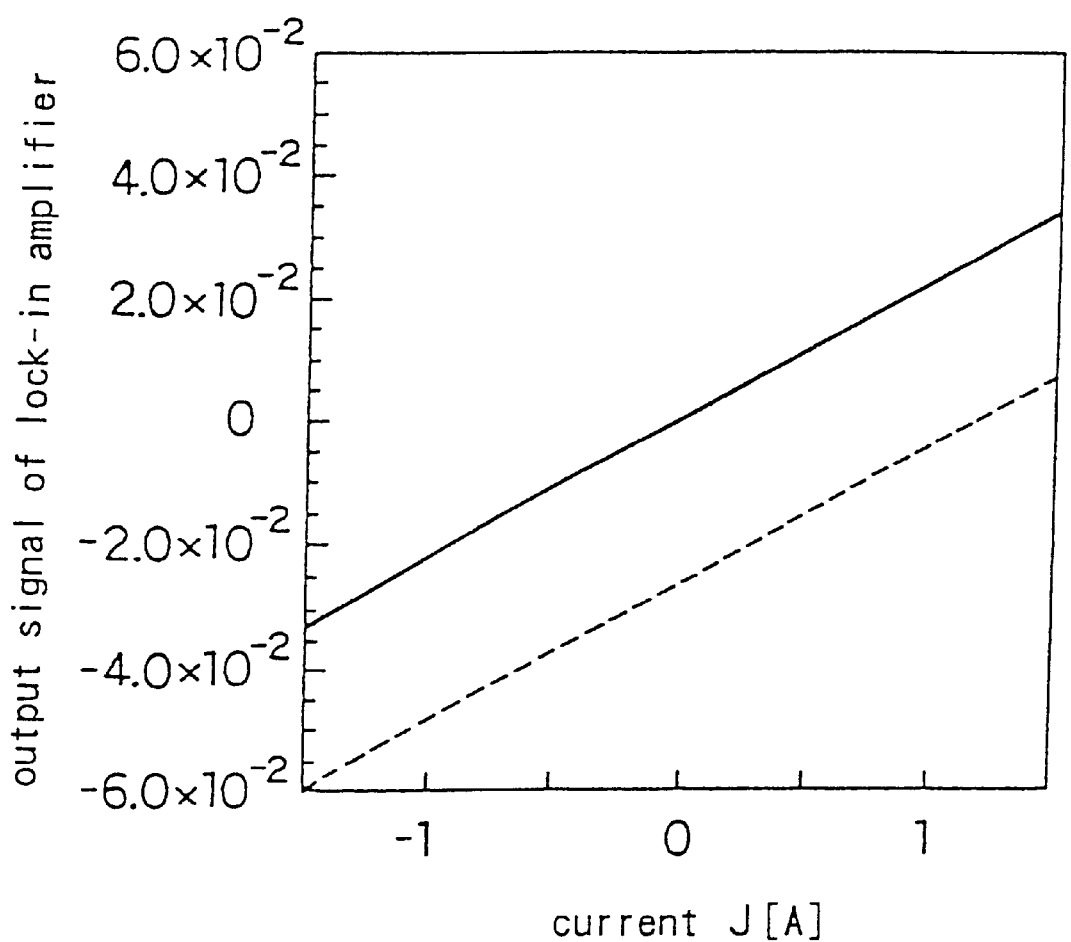
FIG. 13 is a characteristic diagram showing a relation between a current amount J supplied to the solenoid coil and an output signal of a lock-in amplifier obtained by using the same polarimeter.

The operation of the polarimeter will be explained with reference to FIG. 13. The computer 38 issues a command signal to the current source 35, and the current flowing in the solenoid coil 34 is swept from −1.5 to 1.5 A. The resulting output signal of the lock-in amplifier 40 is shown. In the drawing, the abscissa represents the current J flowing in the solenoid coil 34, and the ordinate the output signal (arbitrary value) of the lock-in amplifier 40.

In the diagram, the solid line represents the measurement of pure water having no optically rotatory power. The dotted line, on the other hand, indicates the measurement of the cane sugar aqueous solution having a concentration of 250 mg/dl at 20° C. in temperature as a specimen. An extinction point appears when J=1.21 A. In other words, a new straight line is obtained by translating the solid line by the length of +1.21 A in parallel. This is quantitatively confirmed in a similar manner to the fifth embodiment.

The angle of rotation $\alpha$ due to cane sugar is given from equation (9) as $\alpha = [\alpha]/10000 \times 0.05 \times 250$ $\approx 0.0831$ [degrees]

The rotational angle a of the direction of polarization due to the optical Faraday affect can be calculated from equation (13) as follows.

From the characteristics of the solenoid coil 4', the magnetic field H is given as $6.05 \times 10^3$ A/m when J=1.21 A. This combines with Verdet's constant V of water shown in Table 1 to give $a = 1.645 \times 10^{-2} \times 6.05 \times 10^4 \times 0.05$ $\approx 4.976$ [minutes] $\approx 0.083$ [degrees]

From this, it is confirmed that the angle of rotation of the specimen coincides with the rotational angle due to the optical Faraday effect.

Figure 14:
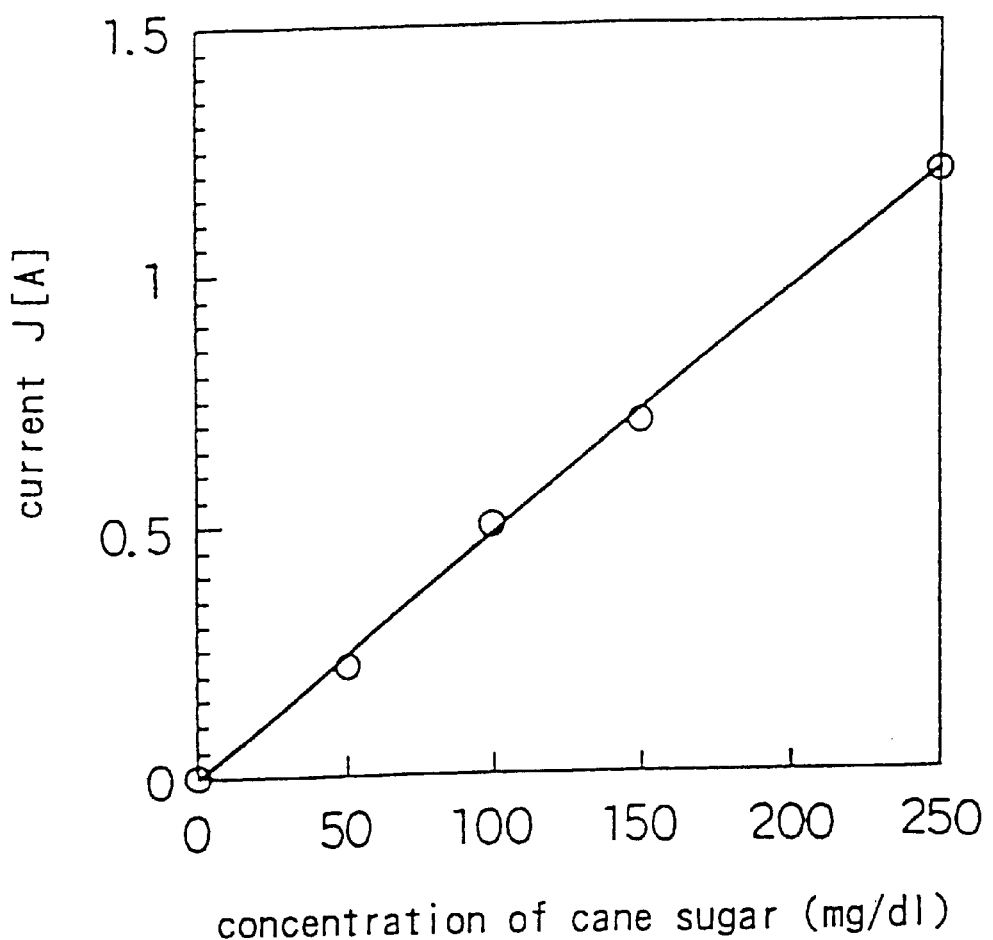
FIG. 14 is a characteristic diagram showing a relation between a concentration of an aqueous solution of cane sugar and an output signal of the light sensor obtained by using the polarimeter.
Figure 15:
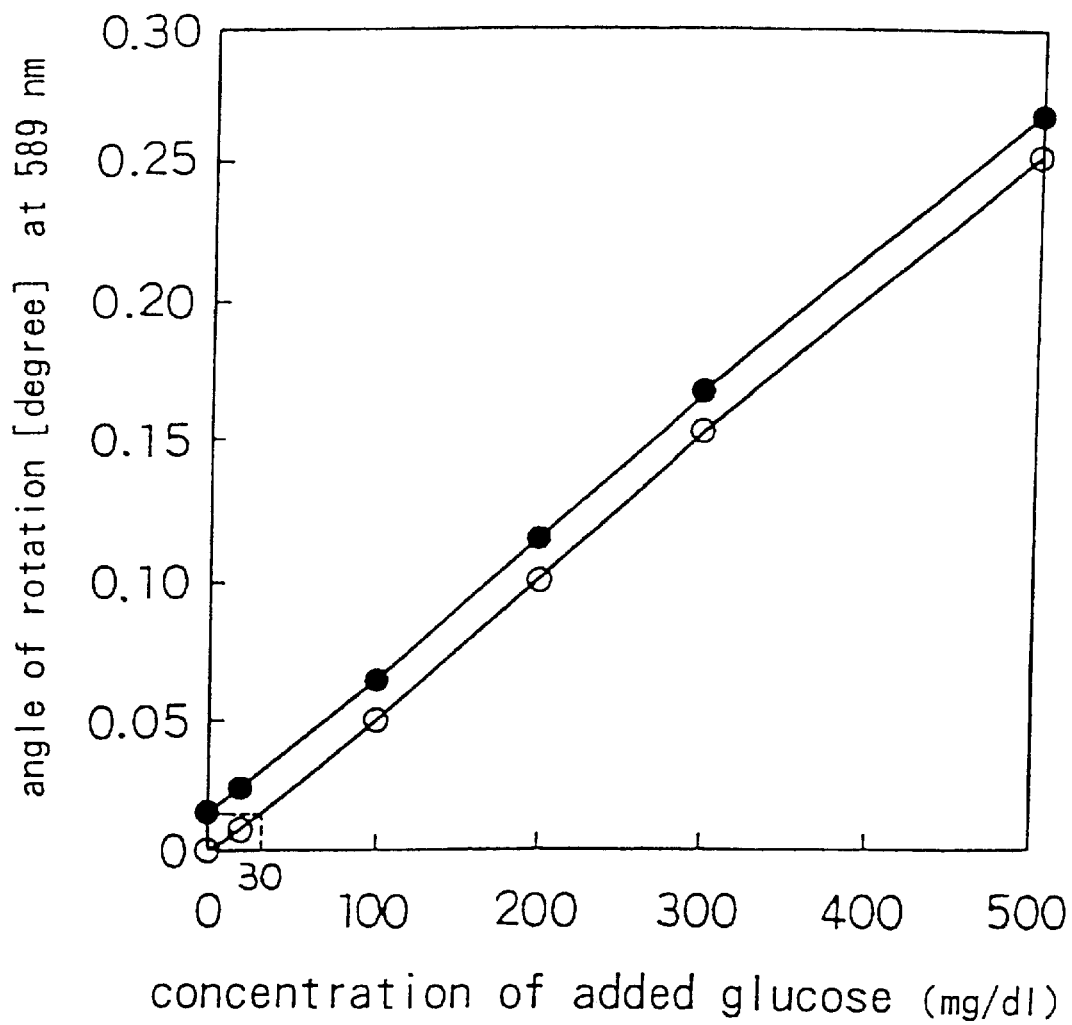
FIG. 15 is a characteristic diagram showing a relation between a glucose concentration of a glucose aqueous solution or a urine with glucose dissolved therein and an angle of rotation obtained by a measurement using the polarimeter.

Further, the angle of rotation of cane sugar aqueous solutions having the concentrations of 50, 100, 150 and 250 mg, respectively, was measured at the temperature of 20° C. using this polarimeter. The result is shown in FIG. 14. This also substantiates the linearity.

With the conventional polarimeter, the analyzer is rotated, and the angle of the analyzer is directly read when the output signal of the lock-in amplifier, i.e., the value S assumes zero. In the polarimeter according to this embodiment, on the other hand, the magnetic field is swept, i.e., the current is swept, and the current value is read when the output signal S of the lock-in amplifier 40 becomes zero, and is further converted into the angle thereby to measure the angle of rotation of the specimen.

According to this embodiment, an extinction point exists in the sweeping range of the magnetic field. However, since the output signal S of the lock-in amplifier 40 changes linearly with respect to the magnetic field, i.e., the current J as shown in FIG. 13 and equation (7), even in the absence of an extinction point within the sweeping range, the angle of rotation can be calculated by extrapolation. Also, since the relation between J and S is linear, continuous sweeping is not necessarily required, and the angle of rotation can be calculated by interpolation or extrapolation from measurements at two or more points in the magnetic field. This enables to shorten a measurement time.

Now, explanation will be made about the case in which the surface of the sample cell through which light is to be transmitted is contaminated after repetitive operations over a long time. If this contamination is caused by an optically inactive substance, it follows that T in equation (1) is substantially reduced. As a result, the position of the extinction point becomes ambiguous for a deteriorated measurement accuracy. In this case, the rate of change of I with respect to $\theta$ in equation (2) and the inclination of S with respect to $\beta$ in equation (7) are reduced. Therefore, the amount of contamination can be detected from these amounts of reduction determined by measuring a reference specimen with a known T. When this amount of contamination exceeds a specified value, an instruction to clean or replace the sample cell can be given. In such a case, the reference specimen is not always necessary, but the contamination can be detected from the measurement of a specimen with a known minimum value of T.

In the case where the contamination is caused by an optically active substance, on the other hand, I in equation (2) and S in equation (7) are translated in parallel in the direction of $\theta$ and $\beta$, respectively. As a result, the position of an extinction point, i.e., the angle of rotation measured is also displaced by the amount of particular translation. This amount of translation represents an angle of rotation due to the contaminating substance and can be simply added to the angle of rotation due to the specimen. Therefore, a reference specimen with a known angle of rotation is measured and the difference between this measurement and the known angle of rotation is calculated, so that the measurement of the specimen is corrected by the difference. As a result, the error caused by the contamination substance can be compensated for.

As described above, by measuring a reference specimen with a known angle of rotation, the error due to the contamination of the sample cell can be compensated. As a result, the time length before cleaning or replacing the sample cell after a long time of repetitive uses can be lengthened considerably until the transmittance of the plane of transmission is reduced to a specified value, thus facilitating maintenance and management. Especially in the case where the apparatus is used as a home urine analyzer, the maintenance and management ease greatly contributes to the extension of its application.

A sample cell left without being cleaned long time and having the plane of transmission contaminated was actually injected with pure water as a specimen, and the angle of rotation of this pure water was measured. In the process, an extinction point was presented at J=0.02 A. As a result, the angle of rotation d due to the substance contaminating the plane of transmission of the sample cell is given from equation (13) and Table 2 as $$d = 1.645 \times 10^{-2} \times 10^2 \times 0.05$$

$$\approx 0.082 \text{ [minutes]} \approx 1.4 \times 10^{-3} \text{ [degrees]}$$

As described above, the error of measurement with a contaminated sample is comparatively small as compared with the angle of rotation exhibited by the specimen. Also, in the case of using such a sample cell, correction is made by subtracting d from the measurement. In the case where the same sample cell is used repetitively over a long time, therefore, a reference specimen with a known angle of rotation, or especially, water exhibiting no optically rotatory power is measured, and the resulting measurement is used to correct the measurement of the specimen thereby making possible highly accurate measurement. This operation can extend the length of time before another cleaning or replacing of the sample cell until the transmittance of the plane of transmission is reduced to a specified value.

Since the function of an optical Faraday modulator obtained by application of a magnetic field to the sample cell as described above eliminates the rotating means as in the fifth embodiment, a compact, inexpensive and highly accurate polarimeter can be realized with a simple configuration.

Also, the polarimeter according to this embodiment permits measurement with a higher accuracy than that of the fifth embodiment, and therefore measurement of the angle of rotation of a solution with a low concentration is also possible. Further, the fact that the light path length can be shortened contributes to a smaller size of the apparatus.

Then, the urine was analyzed using this polarimeter as described below. This examination used a sample cell having a substantial light path length L of 100 mm. First, in order to confirm the performance of this polarimeter against glucose, an analytical curve was prepared. Pure water at 20° C. was prepared together with glucose aqueous solutions 20, 100, 200, 300 and 500 mg/dl in concentration with the pure water as a solvent, then the angle of rotation was measured using these as specimens. The result is shown by white circles in FIG. 19. The abscissa represents the glucose concentration and the ordinate represents the angle of rotation as converted from the current flowing in the solenoid coil 34. The result coincides with that obtained using the specific angle of rotation $[\alpha]=50$ degrees of the 589 nm light for the 20° C., glucose aqueous solution and equation (16).

Then, the angle of rotation was measured of the urine which had been determined to have a glucose concentration of not more than 50 mg/dl arid a concentration of albumin which is urine protein of not more than 10 mg/dl. Further, with this urine as a solvent, glucose solutions, i.e., artificial glycosuria 20, 100, 200, 300 and 500 mg/dl in concentration were prepared. Then, the angle of rotation of these artificial glycosuria was measured. The result is shown by black circles in FIG. 19. The angle of rotation of these artificial glycosuria (black circles) is represented by a straight line translated by $1.5 \times 10^{-2}$ degrees from the analytical line and accurately reflects the glucose concentrations.

The angle of rotation of this urine was $1.5 \times 10^{-2}$ degrees. This is the result of simple addition of the angles of rotation due to the glucose and albumin existing in the urine. The specific angle of rotation $[\alpha]$ of albumin in an aqueous solution at 20° C. for the 589 nm light is $-60$ degrees, which is combined with equation (9) to calculate the range of the angle of rotation A1 of this urine due to the albumin as follows.

$$-60/10000 \times 0.1 \times 10 = -6 \times 10^{-2} \text{ degrees} \leq A1 \leq 0$$

From this relation, the range of the angle of rotation G1 due to glucose is calculated as shown below.

$$1.5 \times 10^{-2} \text{ degrees} \leq G1 \leq 2.1 \times 10^{-2} \text{ degrees}$$

Further, from this value G1, the range of the glucose concentration Cg can be calculated from equation (9) in the manner shown below.

$$30 \text{ mg/dl} \leq Cg \leq 42 \text{ mg/dl}$$

This coincides with the result of the analysis made beforehand.

In similar fashion, the angle of rotation was measured of the urine which had been decided to have a glucose concentration of 300 mg/dl or more and an albumin concentration of 10 mg/dl or less by the urinalysis using the test paper. The result was that the angle of rotation of this urine was $2.2 \times 10^{-2}$ degrees with the glucose concentration Cg determined to be in the range described below.

$$440 \text{ mg/dl} \leq Cg \leq 452 \text{ mg/dl}$$

This also coincides with the analysis made in advance.

In examining the urine having a normal albumin concentration of about 10 mg/dl or less, assume that an abnormal value of the urine glucose level is set to 300 mg/dl or more and that an abnormality is decided when the angle of rotation is not less than $1.5 \times 10^{-1}$ degrees. Then, it follows that an error of only about 12 mg/dl develops.

As described above, the angle of rotation of urine can be measured to determine the concentration of glucose, protein, etc. in the urine simply by placing the urine in the sample cell of the polarimeter and applying a magnetic field to it. As a result, the polarimeter requires no supplies and is easy to maintain and manage and high in reliability, thus realizing a compact and inexpensive urinalysis apparatus.

When this polarimeter is used as a urinalysis apparatus, even in the case where the sample cell is contaminated by the routine urinalysis, the use of the polarimeter under consideration with the urinalysis apparatus makes it is possible to maintain a high measurement accuracy by measuring a reference specimen with a known angle of rotation and correcting the measurement of the specimen involved. As a result of this operation, the time length before cleaning or replacing the sample cell can be extended until the transmittance of the plane of transmission is reduced to a specified value. Especially when it is used as a home urinalysis apparatus, the maintenance and management ease is a great factor for promoting the extension of the use thereof the apparatus.

Although the embodiment described above concerns the examination in which the albumin concentration of the urine examined is low as compared with the glucose concentration thereof, the method mentioned above can also apply with the same effect to analyzing the albumin concentration of the urine low in which this glucose concentration is low as compared with the albumin concentration.

<<Embodiment 7>>

Figure 16:
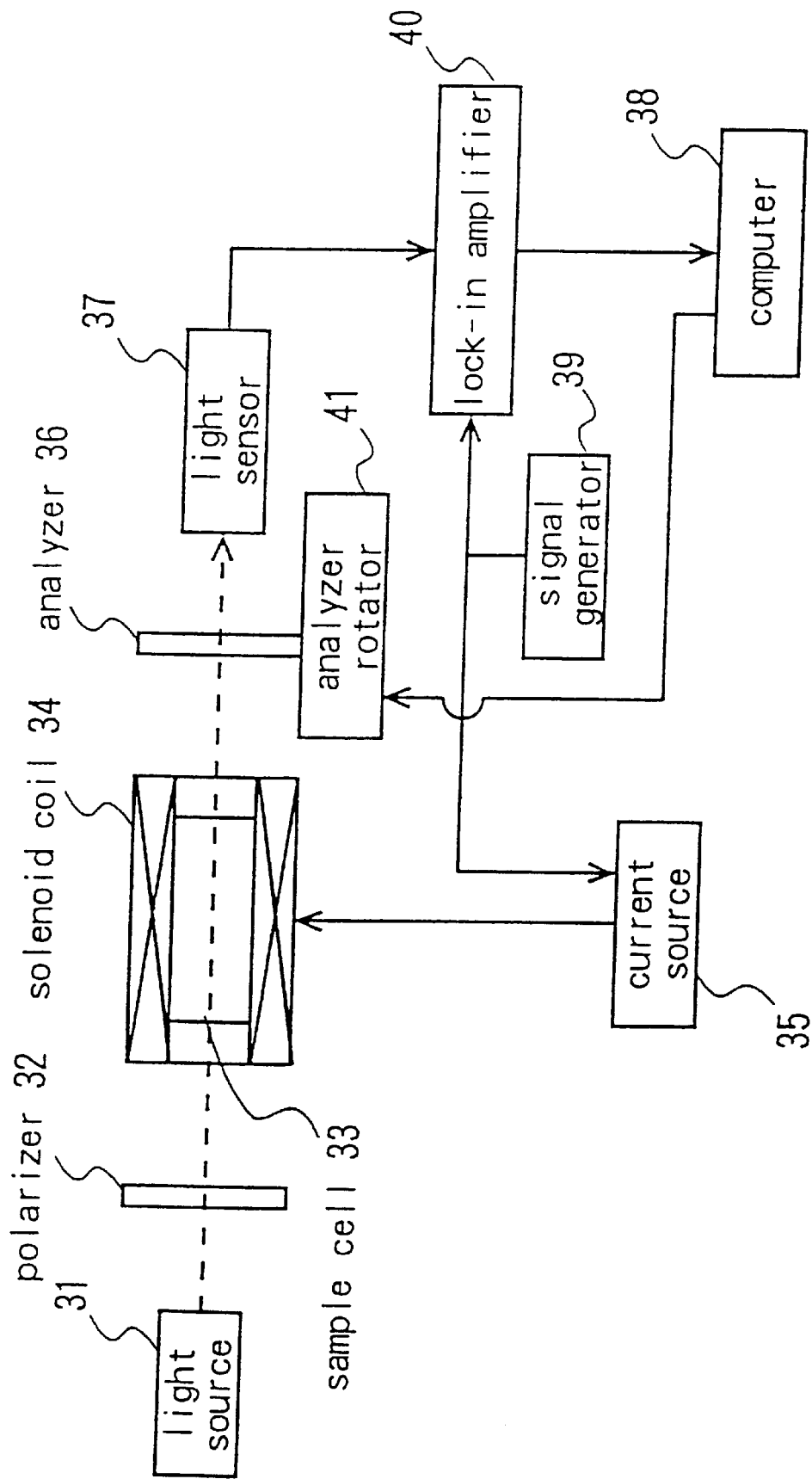
FIG. 16 is a schematic diagram showing a configuration of a polarimeter according to still further embodiment of the present invention.

A polarimeter according to this embodiment will be explained with reference to FIG. 16. In FIG. 16, numerals 31 to 40 designate components similar to the corresponding ones in the sixth embodiment. Nevertheless, the current source 35 converts a modulated signal of 1.3 kHz into a vibration-modulated current signal having an amplitude of 0.02 A, and supplies it to the solenoid coil 33, although the current is not swept. Also, the analyzer rotator 41 rotates the analyzer 36 in response to a command from the computer 38. In this polarimeter, too, the output signal of the lock-in amplifier 40 similarly corresponds to the angular frequency component ω of the output signal of the light sensor 37 in equation (6), i.e., S in equation (7). Therefore, an extinction point is presented when this S becomes zero. The computer 38 issues a command signal to the analyzer rotator 41 thereby to rotate the analyzer 36. When the angle of the analyzer 46 is plotted along the abscissa, and the output signal S of the lock-in amplifier 40 is plotted along the ordinate, a straight line similar to that in FIG. 13 is obtained. The angle of the analyzer 36 when the output signal S of the lock-in amplifier 40 becomes zero corresponds to the angle of rotation of the specimen.

Using this polarimeter, the angle of rotation of cane sugar aqueous solutions having concentrations of 50, 100, 150 and 250 mg/dl, respectively, were measured at 20° C. in temperature as in the fifth embodiment. A similar result was obtained as in FIG. 14.

In the conventional polarimeter, the analyzer is rotated while vibration-modulating the direction of polarization by the optical Faraday modulator, and the angle of the analyzer associated with the time when the output signal of the lock-in amplifier, i.e., S is zero is read directly to measure the angle of rotation of the specimen. With the polarimeter according to this embodiment, on the other hand, a magnetic field is applied to the specimen and vibration-modulated, then, the angle of the analyzer associated with a zero output signal S of the lock-in amplifier is read directly to measure the angle of rotation of the specimen. Thus the embodiment under consideration eliminates the optical Faraday modulator, thereby making it possible to provide a compact, inexpensive polarimeter high in measurement accuracy and reliability. Also, the ease of maintenance and management leads to a very great practical effect of the polarimeter.

As in the sixth embodiment, the relation between the angle of the analyzer and S can be approximated by a linear expression. Therefore, continuous sweep is not necessarily required, but the angle of rotation can be calculated by interpolation or extrapolation based on the measurements at two or more points.

Since polarimeter according to this embodiment, like the polarimeter of the sixth embodiment, can make measurement with a higher accuracy than the polarimeter of the fifth embodiment, the angle of rotation of a solution lower in concentration can also be measured. Further, the fact that a sample cell shorter in light path length can be used contributes to a reduced size of the apparatus <<Embodiment 8>>

Figure 17:
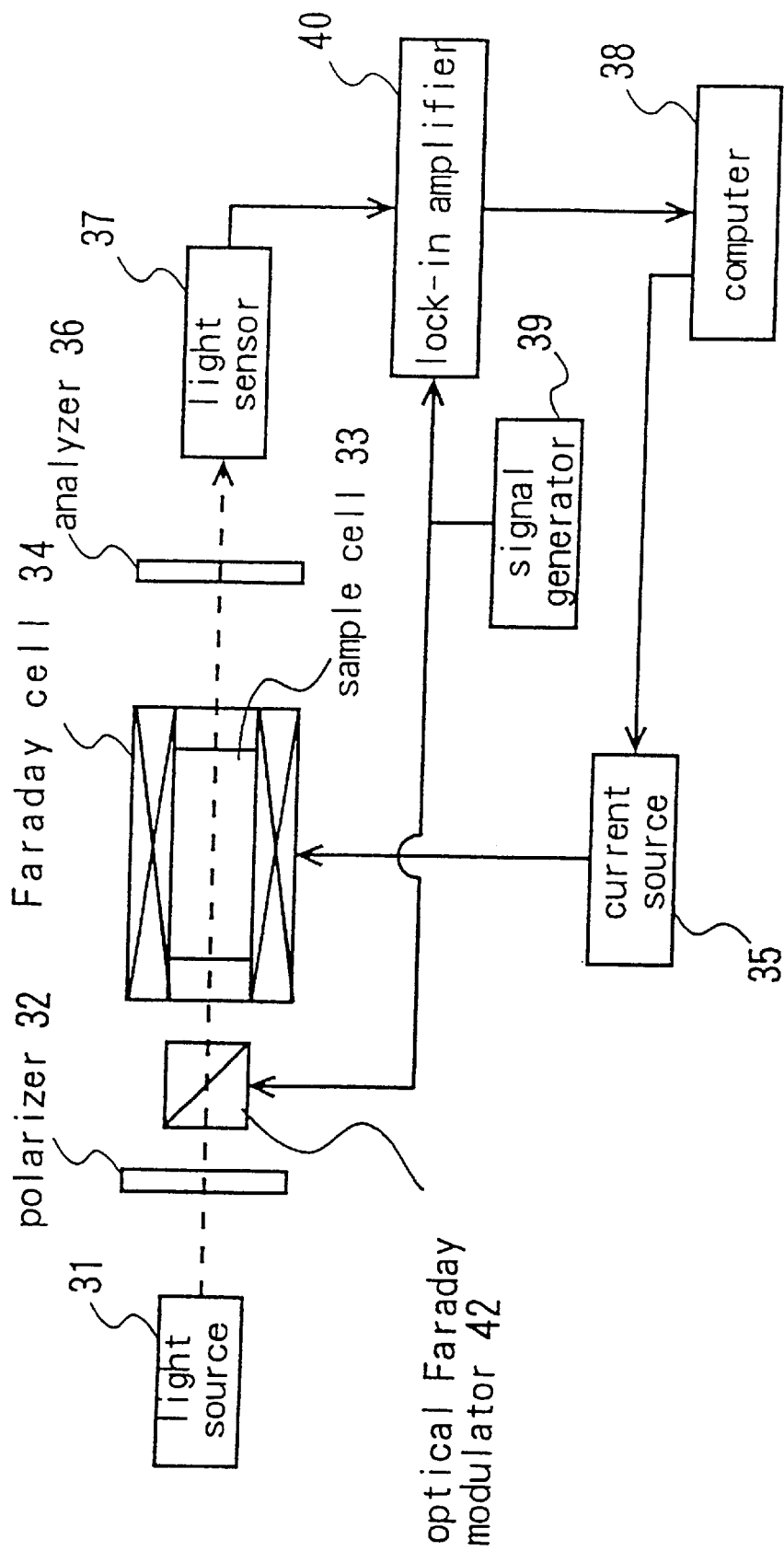
FIG. 17 is a schematic diagram showing a configuration of a polarimeter according to yet still further embodiment of the present invention.

A polarimeter according to this embodiment will be explained with reference to FIG. 17. In FIG. 17, numerals 31 to 40 designate the same component parts which have the same functions as the corresponding ones in the sixth embodiment. The current source 35, however, sweeps the current supplied to the solenoid coil 33 in response to a command from the computer 38. The optical Faraday modulator 42 vibration-modulates the direction of polarization of the light with an amplitude of $1.4 \times 10^{-3}$ degrees by a vibration-modulated signal of 1.3 kHz generated by a signal generator 39. The lock-in amplifier 40 phase-sensitively detects the output signal of the light sensor 37 with reference to the vibration-modulated signal of the signal generator 39.

The output signal of the lock-in amplifier 40 corresponds to the angular frequency component ω of the output signal of the light sensor 37 in equation (6), i.e., S shown in equation (7). Therefore, an extinction point develops when the value S becomes zero.

Now, the operation of this polarimeter will be explained. When the computer 38 issues a command signal to a current source, a current J flowing in the solenoid coil 4 and the output signal (arbitrary value) of the lock-in amplifier 40 were determined, thereby obtaining exactly the same straight line as in FIG. 13. Like in the fifth embodiment, therefore, it was confirmed that the angle of rotation of the specimen coincides with the rotational angle due to the optical Faraday effect.

After measuring the angle of rotation of cane sugar aqueous solutions 50, 100, 150 and 250 mg/dl in concentration at 20° C. in temperature, the same result as in FIG. 14 was obtained. This substantiates the linearity.

According to this embodiment, like in the fifth embodiment, the output signal S of the lock-in amplifier is linearly approximated by the magnetic field, i.e, the current J, therefore continuous sweep is not necessarily required, but the angle of rotation can be calculated by interpolation or extrapolation from the measurements at two or more points in the magnetic field. This also shortens the measurement time.

As described above, according to this embodiment, the direction of polarization is vibration-modulated with a minute amplitude by the optical Faraday modulator, a magnetic field is applied to the specimen, and the magnetic field is swept, thereby eliminating the means of rotating the analyzer, and realizing a compact, inexpensive polarimeter of a great practical value high in accuracy and reliability easy to maintain and manage.

Also, the polarimeter according to this embodiment can measure with a higher accuracy than that of the fifth embodiment, and therefore can measure the angle of rotation of a solution low in concentration. Also, measurement of a specimen with a small light path length thus is possible, which is another factor contributing to a compact apparatus. Although the optical Faraday modulator is used for modulating the direction of polarization in this embodiment, a piezoelectric device can be used in place of the optical Faraday modulator for minute vibratory rotation with a similar effect.

<<Embodiment 9>>

Figure 18:
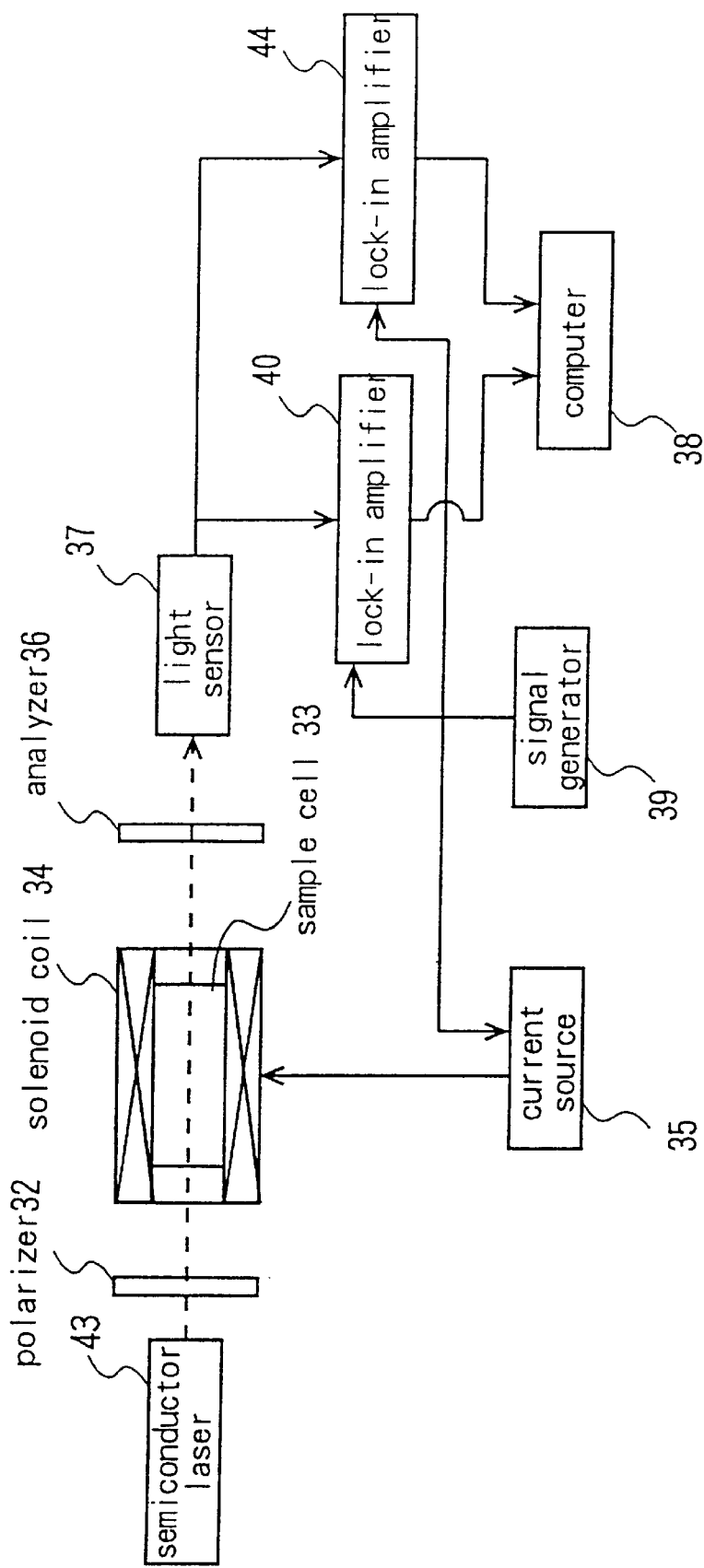
FIG. 18 is a schematic diagram showing a configuration of a polarimeter according to a further embodiment of the present invention.

A polarimeter according to this embodiment will be explained with reference to FIG. 18. In the figure, numerals 32 to 40 designate component parts which are similar and function similarly to the corresponding parts in the sixth embodiment. Nevertheless, a semiconductor laser light source 43 is used instead of the sodium light source. The semiconductor laser light source 43 projects substantially parallel light having a wavelength of 830 nm and an intensity of 10 mW. The current source 35 converts a modulated signal at 1.3 kHz generated by a signal generator 39 into a vibration-modulated signal having an amplitude of 0.02 A, and supplies it to the solenoid coil 44. But the current is not swept unlike in the foregoing embodiment. The lock-in amplifier 34 operates in what is called 2F-mode, and phase-sensitively detects the output signal of the light sensor 37 with reference to a signal having a frequency twice that of the modulated signal of the signal generator 39. Specifically, the lock-in amplifier 34 retrieves the 2×ω component of equation (6). The computer 38 standardizes the output signal of the lock-in amplifier 40 by the output signal of the lock-in amplifier 44 and thus calculates the angle of rotation of the specimen. The principle of this operation is described below.

The output signal of the lock-in amplifier 44 corresponds to S shown in equation (7). Since this value S has a sole function in the case where β is fixed and the values T, $I_O$ and δ are constant as in the present embodiment, therefore, the angle of rotation α can be uniquely calculated from S. Actually, however, T is varied due to the difference in transmittance between specimens, the contamination of the transmission window of the specimen, etc. Also, $I_O$ changes with fluctuations of the source light intensity, and therefore, it is impossible to measure the angle of rotation with high accuracy solely from the value S.

In view of this, the output signal of the lock-in amplifier 44 is utilized. The output signal S' of the lock-in amplifier 44 is given as:

$$S' = T \times I_O \times \delta^2 / 2 \qquad (17)$$

Equation (7) is divided by equation (17) for standardization, then X shown in equation (18) is obtained.

$$X = 4/\delta \times (\beta - \alpha) \qquad (18)$$

Since this X does not contains T and $I_O$, the angle of rotation α can be determined from this relation with high accuracy.

Then, the angle of rotation of glucose aqueous solutions 25, 50, 75 and 100 mg/dl in concentration, respectively, were measured at 20° C. in temperature using this polarimeter. The process is described below.

Figure 19:
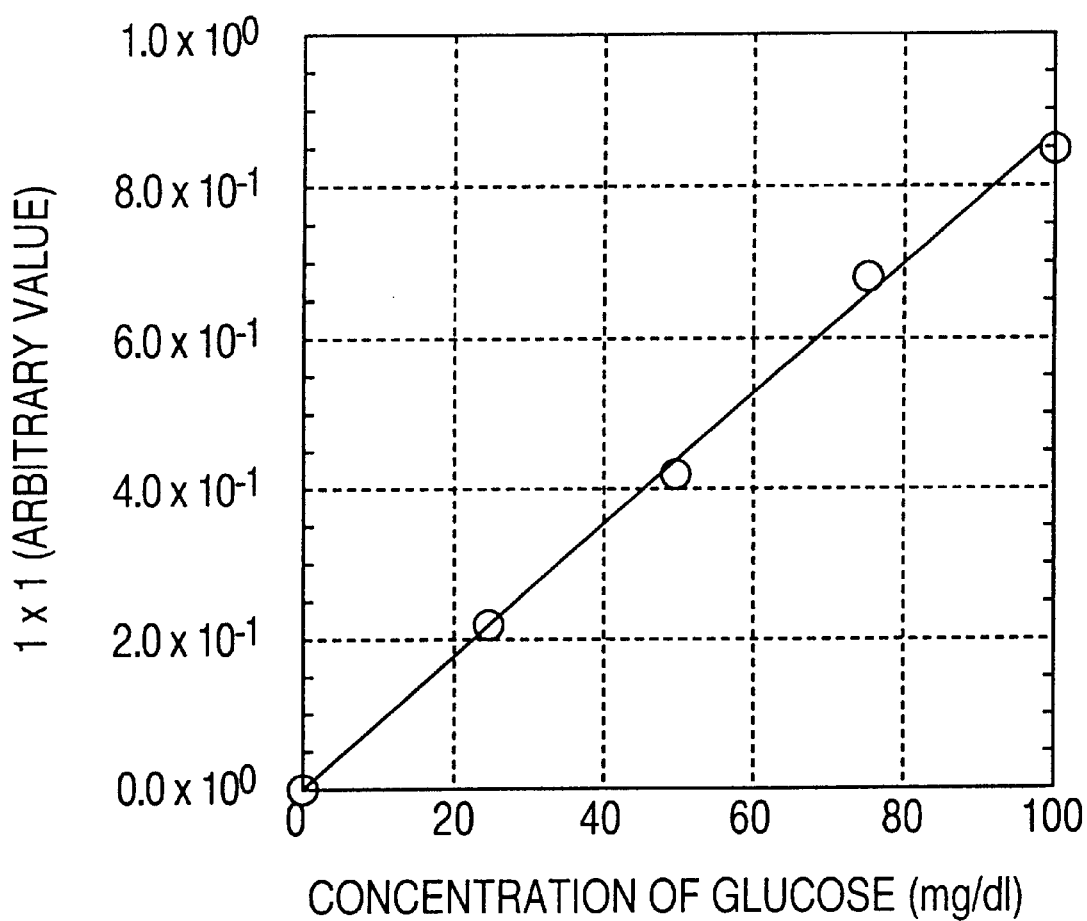
FIG. 19 is a characteristic diagram showing the relation between a standardized variable X and a concentration of an aqueous solution of glucose obtained by using the polarimeter.
Figure 20:
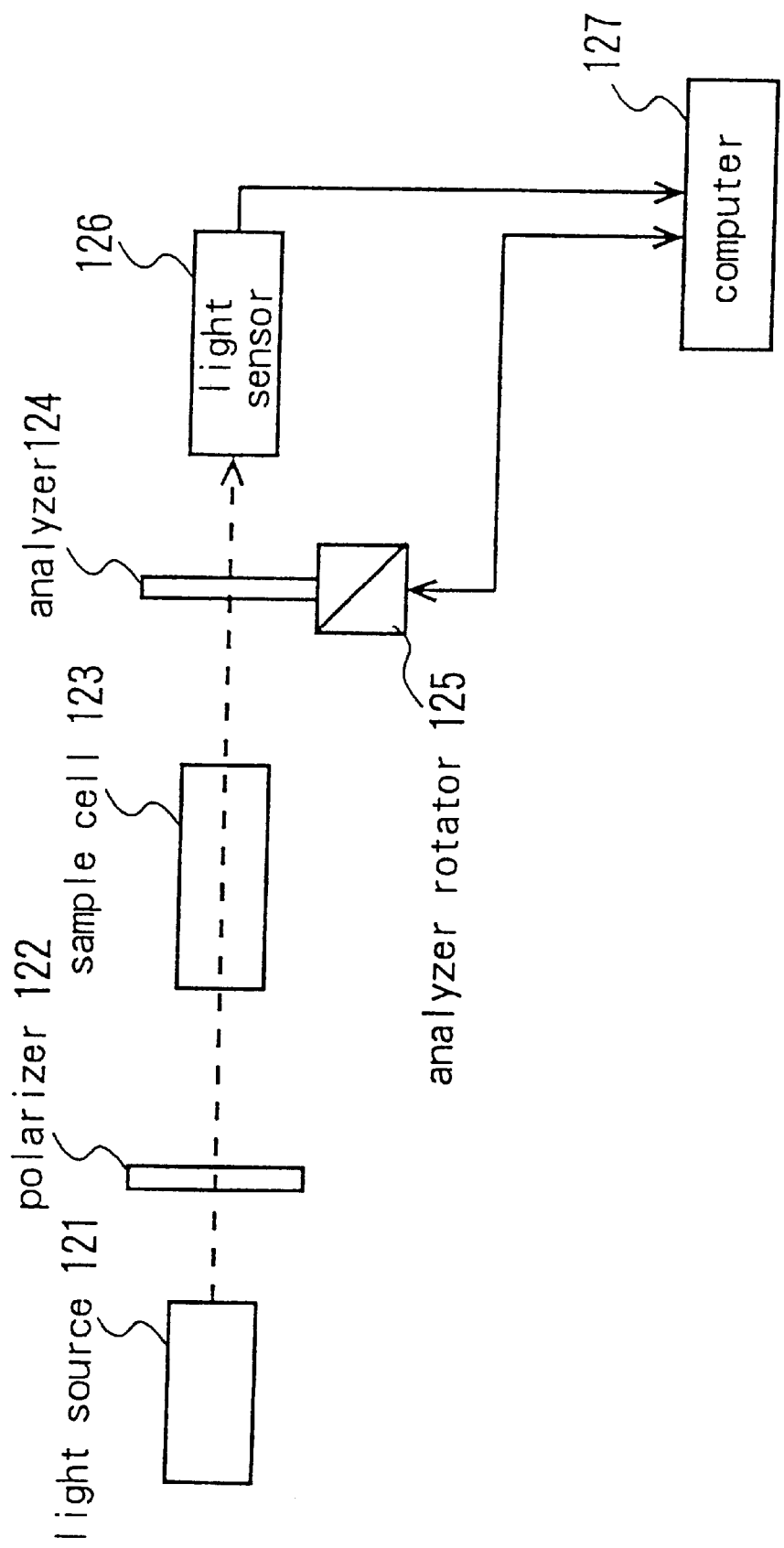
FIG. 20 is a schematic diagram showing a conventional polarimeter.
Figure 21:
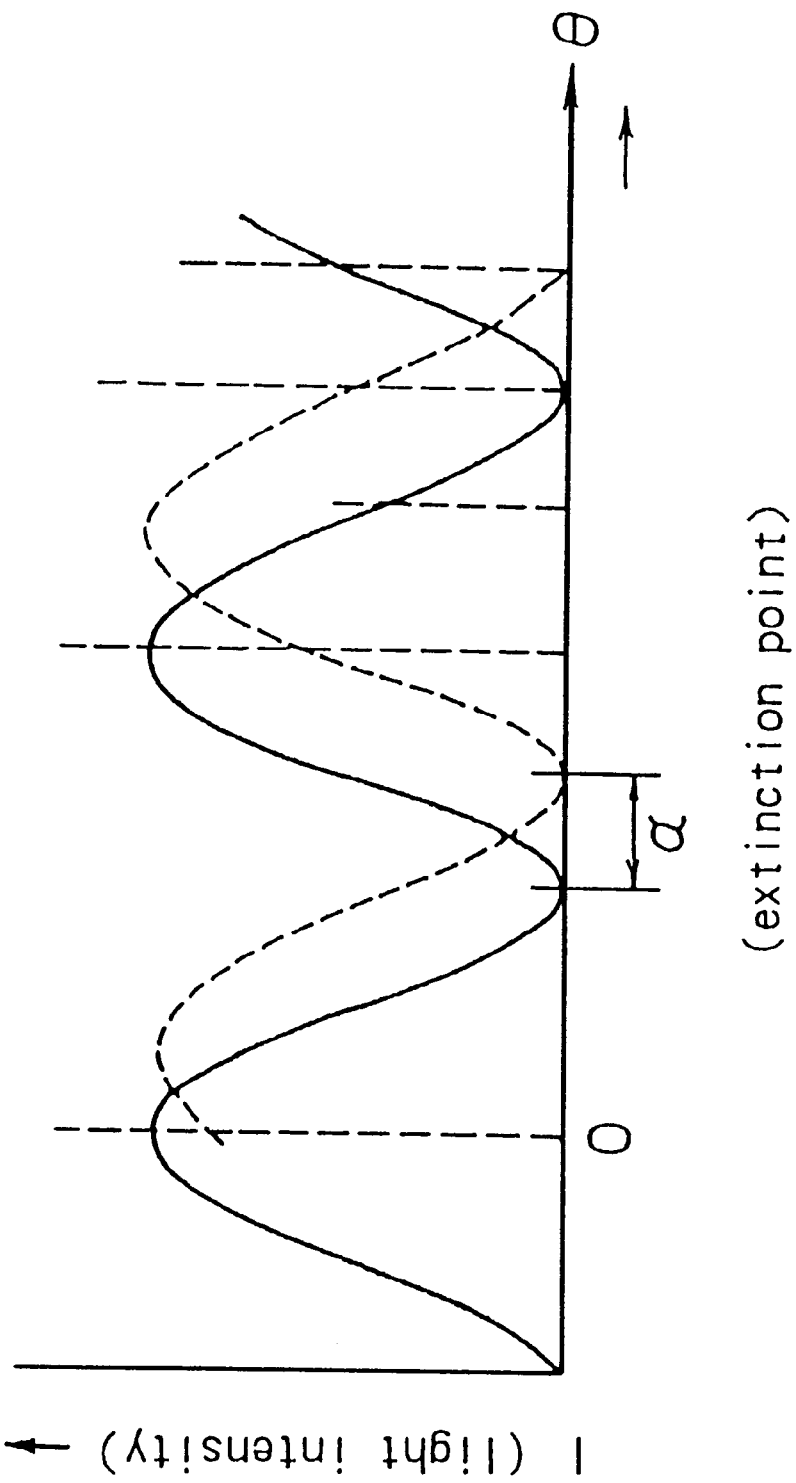
FIG. 21 is a characteristic diagram showing a relation between a rotational angle $\theta$ and a detected light intensity based on the principle of measurement of the polarimeter.
Figure 22:
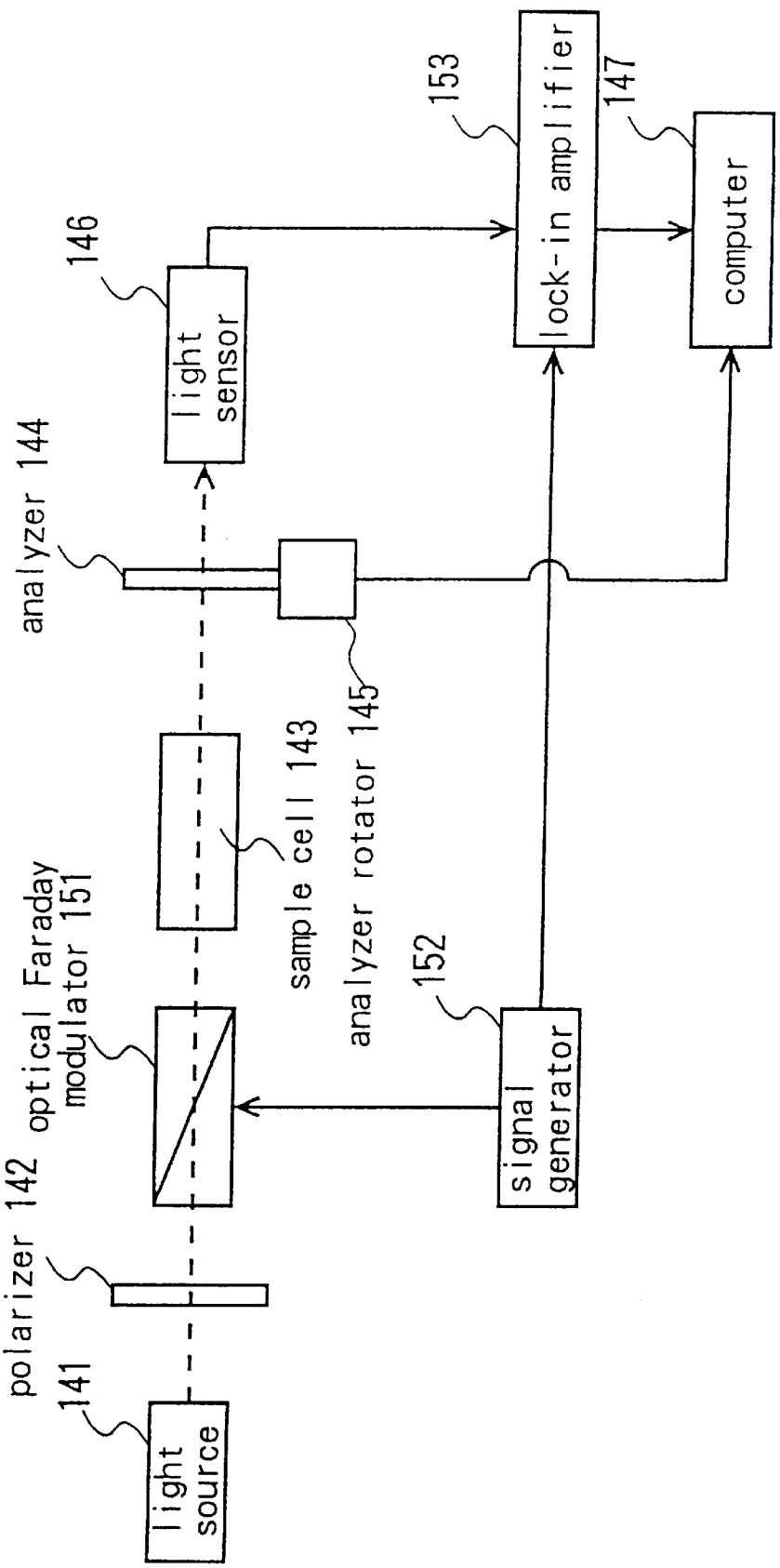
FIG. 22 is a schematic diagram showing another polarimeter.
Figure 23:
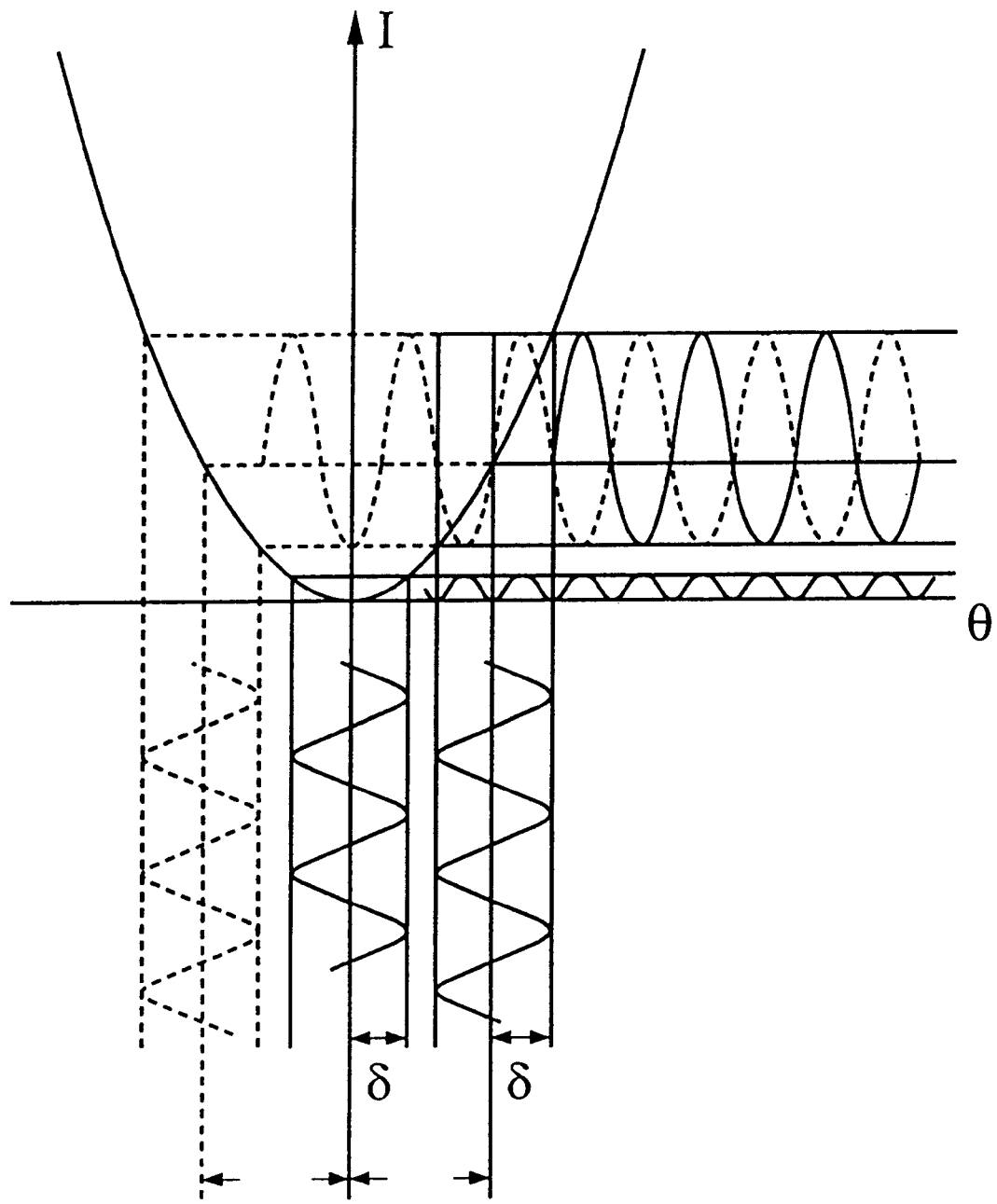
FIG. 23 is a characteristic diagram showing the relation between the rotational angle $\theta$ and the detected light intensity based on the principle of measurement of the polarimeter.

First, pure water is measured as a specimen and the angle of the analyzer 36 is finely adjusted to reduce X to zero. Since the angle of rotation α of pure water is zero, it follows that β is adjusted to zero. The specimen was measured under this condition. When the concentration is plotted along the abscissa and the absolute value of X is plotted along the ordinate, as shown in FIG. 19, a straight line is obtained which is proportional to a and passes through zero. This indicates that the angle of rotation can be measured according to this embodiment. The adjustment of β to zero in advance is not always necessary since the sole purpose of such an adjustment is to determine the magnitude and sign of the angle of rotation of the specimen intuitively as an aid in measurement.

As described above, according to this embodiment, a magnetic field is applied to the specimen and vibration-modulated, and the vibration-modulated frequency component of the output signal of the light sensor is standardized to a value twice the vibration-modulated frequency thereby realizing a compact and inexpensive polarimeter high in accuracy and reliability for a very high practical effect.

Also, the polarimeter according to this embodiment, unlike the polarimeter of the fifth embodiment, requires no sweeping of the current supplied to the solenoid coil. Consequently, the current can be modulated by the source frequency by connecting an appropriate resistor in series to the solenoid coil and connecting the series circuit directly to a 100 V commercial AC power supply. The current source can thus be realized. Although two lock-in amplifiers are needed in this case, since the current source can be considerably simplified, a polarimeter lower in cost thin that of the fifth embodiment may be provided depending on the cost of the current source and the lock-in amplifier.

According to this invention, the angle of rotation is measured on the basis of the position of the extinction point, however, a specified single point such as the brightest point can thus be determined as a reference since this also fulfill the relation of equation (2). In such a case, an optimum point is set taking the linearity and stability of the light sensor and the lock-in amplifier into due consideration.

Industrial Applicability

The invention can be realized as a glycosometer of an optically active detection type for detecting the concentration of aqueous solutions of fruit sugar, cane sugar, glucose, etc. Also, the use of the apparatus for urinalysis, especially for examining the concentration of optically active substances like glucose or protein in urine, is expected to extend widely due to its high reliability, compactness, low cost and other features of high practical value as well as the elimination of the test paper.

According to this invention, a method of urinalysis is provided which is easy to maintain and manage without using supplies such as the test paper.

What is claimed is:

1. A method of urinalysis in which a concentration of an optically active substance in urine is determined, the method comprising the steps of measuring an angle of rotation of said urine, wherein the angle of rotation is measured in the urine containing a substance to be measured having an optical rotary power and an optically active substance of a known concentration; and determining the range of concentration C (kg/dl) of said substance to be measured using the following equation:

$$(A - A_h)/(\alpha \times L) < C < (A - A_1)/(\alpha \times L)$$

$$A_h = L \times a \times C_h$$

$$A_1 = L \times a \times C_1$$

where $A_h$: angle of rotation (degree) of urine measured measured at a maximum value (kg/dl) of concentration of optically active substance of a known concentration, $A_1$: angle of rotation (degree) of urine measured measured at a minimum value (kg/dl) of concentration of optically active substance of a known concentration, $C_h$: maximum value (kg/dl) of concentration of optically active substance of a known concentration, $C_1$: minimum value (kg/dl) of concentration of optically active substance of a known concentration, α: specific angle of rotation (degree/cm·dl/kg) of a substance to be measured, a: specific angle (degree/cm·dl/kg) of rotation of optically active substance of a known concentration, and L: measurement light path length (cm).

2. The method of urinalysis in accordance with claim 1, wherein the urine containing N kinds of optically active substance s is subjected to the measurements of the angle of rotation using the light of at least N kinds of wavelengths, respectively, to determine the concentrations of optically active substances in said urine, N being more than one.

3. The method of urinalysis in accordance with claim 1, wherein the concentration of said optically active substance and the concentration of a light scattering substance in said urine are determined by measuring a quantity of light scattered by said urine in addition to the measurement of the angle of rotation of said urine.

4. The method of urinalysis in accordance with claim 1, wherein said optically active substance is at least one selected from the group consisting of protein, sugar and L-ascorbic acid.

5. The method of urinalysis in accordance with claim 1, wherein said angle of rotation of the urine is measured with respect to the light having a wavelength of 500 nm or more.

* * * * *